(12) United States Patent
Pavcnik et al.

(10) Patent No.: US 9,332,977 B2
(45) Date of Patent: May 10, 2016

(54) CLOSURE DEVICE

(71) Applicants: Cook Medical Technologies LLC, Bloomington, IN (US); Oregon Health and Science University, Portland, OR (US)

(72) Inventors: Dusan Pavcnik, Portland, OR (US); Kurt J. Tekulve, Ellettsville, IN (US); Michael Deckard, Solsberry, IN (US)

(73) Assignees: Cook Medical Technologies LLC, Bloomington, IN (US); Oregon Health and Science University, Portland, OR (US)

( * ) Notice: Subject to any disclaimer, the term of this patent is extended or adjusted under 35 U.S.C. 154(b) by 246 days.

(21) Appl. No.: 14/076,024

(22) Filed: Nov. 8, 2013

(65) Prior Publication Data
US 2014/0066980 A1 Mar. 6, 2014

Related U.S. Application Data

(60) Division of application No. 12/813,489, filed on Jun. 10, 2010, now Pat. No. 8,617,205, which is a continuation-in-part of application No. 12/533,731, filed on Jul. 31, 2009, which is a continuation of (Continued)

(51) Int. Cl.
*A61B 17/08* (2006.01)
*A61B 17/00* (2006.01)
(Continued)

(52) U.S. Cl.
CPC .............. *A61B 17/0057* (2013.01); *A61B 10/06* (2013.01); *A61B 19/54* (2013.01); *A61B 2017/00243* (2013.01); *A61B 2017/00526* (2013.01);
(Continued)

(58) Field of Classification Search
None
See application file for complete search history.

(56) References Cited

U.S. PATENT DOCUMENTS 3,012,882 A 12/1961 Muldawer et al.
3,174,851 A 3/1965 Buechler et al.
(Continued)

FOREIGN PATENT DOCUMENTS

EP 1 281 355 A2 2/2003
EP 1 281 355 A3 2/2003
(Continued)

OTHER PUBLICATIONS

Babic, Uros U., et al., "*Transcatheter Closure of Atrial Septal Defects*", The Lancet, Sep. 1, 1990, pp. 566-567.
(Continued)

*Primary Examiner* — Robert Lynch
(74) *Attorney, Agent, or Firm* — Brinks Gilson & Lione

(57) ABSTRACT

A closure device for closing a bodily passageway is provided. The device includes first and second frames and first and second crossbars. A sheet of biocompatible material is attached to one or more of the frames. The first crossbar extends across the first frame and has terminal crossbar ends connectively linked to separate sites on the first frame; the second crossbar is similarly linked to the second frame. The crossbars are attached to each other at a connection point, and they are each configured to bend away from the connection point when the closure device is deployed to close a bodily passageway. A method of making the closure device is provided, as well as a method for closing a bodily passageway using such a device. Further, a closure device assembly is provided, including a closure device, a delivery catheter housing, and a delivery release member.

10 Claims, 26 Drawing Sheets

Related U.S. Application Data application No. PCT/US2008/001422, filed on Feb. 1, 2008.

(60) Provisional application No. 60/898,834, filed on Feb. 1, 2007.

(51) Int. Cl.
  *A61B 10/06* (2006.01)
  *A61B 19/00* (2006.01)

(52) U.S. Cl.
  CPC .................. *A61B2017/00575* (2013.01); *A61B 2017/00584* (2013.01); *A61B 2017/00592* (2013.01); *A61B 2017/00597* (2013.01); *A61B 2017/00606* (2013.01); *A61B 2017/00623* (2013.01); *Y10T 29/49826* (2015.01)

(56) References Cited

U.S. PATENT DOCUMENTS

| | | |
|---|---|---|
| 3,772,137 A | 11/1973 | Toliver |
| 3,953,566 A | 4/1976 | Gore |
| 4,665,906 A | 5/1987 | Jervis |
| 4,675,361 A | 6/1987 | Ward, Jr. |
| 4,836,204 A | 6/1989 | Landymore et al. |
| 4,861,830 A | 8/1989 | Ward, Jr. |
| 4,911,163 A | 3/1990 | Fina |
| 4,917,089 A | 4/1990 | Sideris |
| 5,017,664 A | 5/1991 | Grasel et al. |
| 5,020,612 A | 6/1991 | Williams |
| 5,024,671 A | 6/1991 | Tu et al. |
| 5,108,420 A | 4/1992 | Marks |
| 5,167,628 A | 12/1992 | Boyles |
| 5,176,692 A | 1/1993 | Wilk et al. |
| 5,192,301 A | 3/1993 | Kamiya et al. |
| 5,258,000 A | 11/1993 | Gianturco |
| 5,284,488 A | 2/1994 | Sideris |
| 5,334,217 A | 8/1994 | Das |
| 5,417,708 A | 5/1995 | Hall et al. |
| 5,425,744 A | 6/1995 | Fagan et al. |
| 5,433,727 A | 7/1995 | Sideris |
| 5,451,235 A | 9/1995 | Lock et al. |
| 5,486,195 A | 1/1996 | Myers et al. |
| 5,589,563 A | 12/1996 | Ward et al. |
| 5,595,571 A | 1/1997 | Jaffe et al. |
| 5,634,936 A | 6/1997 | Linden et al. |
| 5,643,317 A | 7/1997 | Pavcnik et al. |
| 5,669,933 A | 9/1997 | Simon et al. |
| 5,683,411 A | 11/1997 | Kavteladze et al. |
| 5,690,642 A | 11/1997 | Osborne et al. |
| 5,702,421 A | 12/1997 | Schneidt |
| 5,709,707 A | 1/1998 | Lock |
| 5,720,777 A | 2/1998 | Jaffe et al. |
| 5,725,534 A | 3/1998 | Rasmussen |
| 5,733,337 A | 3/1998 | Carr, Jr. et al. |
| 5,769,796 A | 6/1998 | Palermo et al. |
| 5,772,632 A | 6/1998 | Forman |
| 5,797,953 A | 8/1998 | Tekulve |
| 5,797,960 A | 8/1998 | Stevens et al. |
| 5,814,061 A | 9/1998 | Osborne et al. |
| 5,843,180 A | 12/1998 | Jaffe et al. |
| 5,843,181 A | 12/1998 | Jaffe et al. |
| 5,846,247 A | 12/1998 | Unsworth et al. |
| 5,846,261 A | 12/1998 | Kolula et al. |
| 5,853,422 A | 12/1998 | Huebsch et al. |
| 5,861,003 A | 1/1999 | Latson et al. |
| 5,879,366 A | 3/1999 | Shaw et al. |
| 5,944,738 A | 8/1999 | Amplatz et al. |
| 5,947,997 A | 9/1999 | Pavcnik et al. |
| 5,960,642 A | 10/1999 | Kim et al. |
| 5,980,799 A | 11/1999 | Martakos et al. |
| 5,993,844 A | 11/1999 | Abraham et al. |
| 6,063,113 A | 5/2000 | Kavteladze et al. |
| 6,077,281 A | 6/2000 | Das |
| 6,077,291 A | 6/2000 | Das |
| 6,080,182 A | 6/2000 | Shaw et al. |
| 6,113,623 A | 9/2000 | Sgro |
| 6,117,157 A | 9/2000 | Tekulve |
| 6,117,159 A | 9/2000 | Huebsch et al. |
| 6,174,322 B1 | 1/2001 | Schneidt |
| 6,193,731 B1 | 2/2001 | Oppelt et al. |
| 6,206,907 B1 | 3/2001 | Marino et al. |
| 6,206,931 B1 | 3/2001 | Cook et al. |
| 6,214,029 B1 | 4/2001 | Thill et al. |
| 6,238,416 B1 | 5/2001 | Sideris |
| 6,296,657 B1 | 10/2001 | Brucker |
| 6,346,074 B1 | 2/2002 | Roth |
| 6,355,052 B1 | 3/2002 | Neuss et al. |
| 6,358,228 B1 | 3/2002 | Tubman et al. |
| 6,358,284 B1 | 3/2002 | Fearnot et al. |
| 6,368,338 B1 | 4/2002 | Konya et al. |
| 6,371,961 B1 | 4/2002 | Osborne et al. |
| 6,379,368 B1 | 4/2002 | Corcoran et al. |
| 6,451,052 B1 | 9/2002 | Burmeister et al. |
| 6,458,137 B1 | 10/2002 | Klint |
| 6,547,815 B2 | 4/2003 | Myers |
| 6,572,650 B1 | 6/2003 | Abraham et al. |
| 6,623,508 B2 | 9/2003 | Shaw et al. |
| 6,656,206 B2 | 12/2003 | Corcoran et al. |
| 6,673,100 B2 | 1/2004 | Diaz et al. |
| 6,692,458 B2 | 2/2004 | Forman et al. |
| 6,749,622 B2 | 6/2004 | McGuckin, Jr. et al. |
| 6,752,826 B2 | 6/2004 | Holloway et al. |
| 6,783,499 B2 | 8/2004 | Schwartz |
| 6,790,218 B2 | 9/2004 | Jayaraman |
| 6,911,037 B2 | 6/2005 | Gainor et al. |
| 6,939,377 B2 | 9/2005 | Jayaraman et al. |
| 6,949,113 B2 | 9/2005 | Van Tassel et al. |
| 6,949,116 B2 | 9/2005 | Solymar et al. |
| 6,960,220 B2 | 11/2005 | Marino et al. |
| 6,974,474 B2 | 12/2005 | Pavcnik et al. |
| 6,994,092 B2 | 2/2006 | Van der Burg et al. |
| 6,994,717 B2 | 2/2006 | Konya et al. |
| 7,101,381 B2 | 9/2006 | Ford et al. |
| 7,101,395 B2 | 9/2006 | Tremulis et al. |
| 7,128,073 B1 | 10/2006 | Van der Burg et al. |
| 7,144,410 B2 | 12/2006 | Marino et al. |
| 7,288,105 B2 | 10/2007 | Oman et al. |
| 8,366,741 B2 | 2/2013 | Chin et al. |
| 8,366,743 B2 | 2/2013 | Zeng et al. |
| 2001/0034537 A1 | 10/2001 | Shaw et al. |
| 2001/0037129 A1 | 11/2001 | Thill |
| 2001/0039450 A1 | 11/2001 | Pavcnik et al. |
| 2002/0111647 A1 | 8/2002 | Khairkhahan et al. |
| 2002/0169475 A1 | 11/2002 | Gainor et al. |
| 2002/0183787 A1 | 12/2002 | Wahr et al. |
| 2002/0187288 A1 | 12/2002 | Lim et al. |
| 2002/0198563 A1 | 12/2002 | Gainor et al. |
| 2003/0028213 A1 | 2/2003 | Thill et al. |
| 2003/0093108 A1 | 5/2003 | Avellanet et al. |
| 2003/0130713 A1 | 7/2003 | Stewart et al. |
| 2003/0139819 A1 | 7/2003 | Beer et al. |
| 2003/0144694 A1 | 7/2003 | Chanduszko et al. |
| 2003/0149471 A1 | 8/2003 | Briana et al. |
| 2003/0191495 A1 | 10/2003 | Ryan et al. |
| 2003/0206860 A1 | 11/2003 | Bleyer et al. |
| 2004/0073242 A1 | 4/2004 | Chanduszko |
| 2004/0078053 A1 | 4/2004 | Berg et al. |
| 2004/0093017 A1 | 5/2004 | Chanduszko |
| 2004/0098030 A1 | 5/2004 | Makower et al. |
| 2004/0098042 A1 | 5/2004 | Devellian et al. |
| 2004/0133236 A1 | 7/2004 | Chanduszko |
| 2004/0143277 A1 | 7/2004 | Marino et al. |
| 2004/0143291 A1 | 7/2004 | Corcoran et al. |
| 2004/0143292 A1 | 7/2004 | Marino et al. |
| 2004/0143293 A1 | 7/2004 | Marino et al. |
| 2004/0143294 A1 | 7/2004 | Corcoran et al. |
| 2004/0166169 A1 | 8/2004 | Malaviya et al. |
| 2004/0176799 A1 | 9/2004 | Chanduszko et al. |
| 2004/0213756 A1 | 10/2004 | Michael et al. |
| 2004/0220596 A1 | 11/2004 | Frazier et al. |
| 2004/0220610 A1 | 11/2004 | Kreidler et al. |
| 2004/0230222 A1 | 11/2004 | Van der Burg et al. |

(56) References Cited

U.S. PATENT DOCUMENTS

| | | |
|---|---|---|
| 2004/0260340 A1 | 12/2004 | Jacobs et al. |
| 2004/0267191 A1 | 12/2004 | Gifford, III et al. |
| 2004/0267306 A1 | 12/2004 | Blaeser et al. |
| 2005/0010248 A1 | 1/2005 | Lafontaine et al. |
| 2005/0034735 A1 | 2/2005 | Deem et al. |
| 2005/0043759 A1 | 2/2005 | Chanduszko |
| 2005/0049634 A1 | 3/2005 | Chopra |
| 2005/0065547 A1 | 3/2005 | Marino et al. |
| 2005/0065548 A1 | 3/2005 | Marino et al. |
| 2005/0070794 A1 | 3/2005 | Deal et al. |
| 2005/0070821 A1 | 3/2005 | Deal et al. |
| 2005/0085843 A1 | 4/2005 | Opolski et al. |
| 2005/0125032 A1 | 6/2005 | Whisenant et al. |
| 2005/0125050 A1 | 6/2005 | Carter et al. |
| 2005/0192626 A1 | 9/2005 | Widomski et al. |
| 2005/0192627 A1 | 9/2005 | Whisenant et al. |
| 2005/0203568 A1 | 9/2005 | Burg et al. |
| 2005/0228434 A1 | 10/2005 | Amplatz et al. |
| 2005/0234509 A1 | 10/2005 | Widomski et al. |
| 2005/0249772 A1 | 11/2005 | Malaviya et al. |
| 2005/0251154 A1 | 11/2005 | Chanduszko et al. |
| 2005/0251201 A1 | 11/2005 | Roue et al. |
| 2005/0256532 A1 | 11/2005 | Nayak et al. |
| 2005/0267524 A1 | 12/2005 | Chanduszko |
| 2005/0267526 A1 | 12/2005 | Wahr et al. |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0283187 A1 | 12/2005 | Longson |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0036282 A1 | 2/2006 | Wahr et al. |
| 2006/0052816 A1 | 3/2006 | Bates et al. |
| 2006/0052821 A1 | 3/2006 | Abbott et al. |
| 2006/0106418 A1 | 5/2006 | Seibold et al. |
| 2006/0106420 A1 | 5/2006 | Dolan et al. |
| 2006/0122646 A1 | 6/2006 | Corcoran et al. |
| 2006/0155327 A1 | 7/2006 | Briganti et al. |
| 2006/0200196 A1 | 9/2006 | Zang et al. |
| 2006/0201996 A1 | 9/2006 | Hodde |
| 2006/0210603 A1 | 9/2006 | Williams et al. |
| 2006/0216326 A1 | 9/2006 | Pacetti |
| 2006/0217760 A1 | 9/2006 | Widomski et al. |
| 2006/0217761 A1 | 9/2006 | Opolski |
| 2006/0229670 A1 | 10/2006 | Bates |
| 2006/0235467 A1 | 10/2006 | Devore |
| 2006/0241687 A1 | 10/2006 | Glaser et al. |
| 2006/0271030 A1 | 11/2006 | Francis et al. |
| 2008/0091235 A1 | 4/2008 | Sirota |
| 2009/0062836 A1 | 3/2009 | Kurrus |
| 2009/0062844 A1 | 3/2009 | Tekulve et al. |
| 2010/0030246 A1 | 2/2010 | Pavcnik et al. |
| 2010/0030259 A1 | 2/2010 | Pavcnik et al. |
| 2013/0116720 A1 | 5/2013 | Theobald et al. |

FOREIGN PATENT DOCUMENTS

| | | |
|---|---|---|
| EP | 1 281 355 B1 | 9/2005 |
| JP | 02-307480 | 12/1990 |
| WO | WO 93/10714 | 6/1993 |
| WO | WO 98/27868 | 7/1998 |
| WO | WO 2007/092274 A1 | 8/2007 |

OTHER PUBLICATIONS

Bhattathiri, VN, et al., "*Influence of plasma GSH level on acute radiation mucositis of the oral cavity*", International Journal of Radiation Oncology Biology Physics, (1994), vol. 29, No. 2, pp. 383-386.

Braun, M., et al., "*Transcatheter Closure of Patent Foramen Ovale (PFO) in Patients With Paradoxical Embolism*", European Heart Journal (2004), vol. 25, pp. 424-430.

ISR/Written Opinion of PCT/US2008/001422, dated Aug. 4, 2009, (14p).

Das, Gladwin S., et al., "*Experimental Atrial Septal Defect Closure With a New, Transcatheter, Self-Centering Device*", Circulation, vol. 88, No. 4, Part 1, Oct. 1993, pp. 1754-1764.

Heeschen, Christopher, et al., "*Nicotine Stimulates Angiogenesis and Promotes Tumor Growth and Atherosclerosis*", Nature Medicine vol. 7, No. 7, (Jul. 2001), pp. 833-839.

Johnson, Chad, et al., "*Matrix Metalloproteinase-9 is Required for Adequate Angiogenic Revascularization of Ischemic Tissues*", Circulation Research, Feb. 6, 2004, No. 94, pp. 262-268.

Jux, Christian, et al., "*A New Biological Matrix for Septal Occlusion*", Journal of Interventional Cardiology, vol. 16, No. 2, (2003), pp. 149-152.

Jux, Christian, et al., "*Interventional Atrial Septal Defect Closure Using a Totally Bioresorbable Occluder Matrix*", JACC, vol. 48, No. 1, (2006), pp. 161-169.

King, Terry D., et al., "*Secundum Atrial Septet Defect-Nonoperative Closure During Cardiac Catheterization*", JAMA, vol. 235, No. 23, Jun. 7, 1978, pp. 2506-2509.

Mullen, Michael J., et al., "*BioSTAR Evaluation STudy (BEST) A Prospective, Multicenter, Phase I Clinical Trial to Evaluate the Feasibility, Efficacy, and Safety of the BioSTAR Bioabsorbable Septal Repair Implant for the Closure of Atrial-Level Shunts*", Circulation, Oct. 31, 2006, pp. 1962-1967.

Oguchi, M., et al., "*Mucosa-adhesive water-soluble polymer film for treatment of acute radiation-induced oral mucositis*", International Journal of Radiation Oncology Biology Physics, Mar. 15, 1998, vol. 40, No. 5, p. 1033-1037.

Pavcnik, Dusan et al., "*Monodisk: Device for Percutaneous Transcatheter Closure of Cardiac Septal Defects*", Cardiovasc Intervent Radiol (1993) vol. 16, pp. 308-312.

Rashkind, William J., "*Transcatheter Treatment of Congenital Heart Disease*", Circulation vol. 67, No. 4, Apr. 1983, pp. 711-716.

Sideris, E.B. et al., "*Transvenous Atrial Septal Defect Occlusion in Piglets with a "Buttoned" Double-Disk Device*", Circulation, vol. 81, No. 1, Jan. 1990, pp. 312-318.

CLOSURE DEVICE

CROSS-REFERENCE TO RELATED APPLICATIONS

This application is a division of U.S. patent application Ser. No. 12/813,489, filed Jun. 10, 2010, which is a continuation-in-part of U.S. patent application Ser. No. 12/533,731, published as U.S. publication no. 2010/0030259, filed on Jul. 31, 2009, which is a continuation of PCT application no. PCT/US2008/001422, filed on Feb. 1, 2008, which claims the benefit of priority under 35 U.S.C. §119(e) to U.S. Provisional Application No. 60/898,834, filed Feb. 1, 2007, all of which are hereby incorporated by reference in their entireties.

TECHNICAL FIELD

This invention relates generally to medical devices, and particularly, to implantable medical devices for closing bodily passageways, including the patent foramen ovale (PFO) and various atrial septal defects (ASDs).

BACKGROUND

A patent foramen ovale is a persistent, one-way, usually flap-like opening in the wall between the right atrium and left atrium of the heart. In utero, the foramen ovale serves as a physiologic conduit for right-to-left shunting of blood in the fetal heart. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure presses the septum primum against the walls of the septum secundum, covering the foramen ovale and resulting in functional closure of the foramen ovale. This closure is usually followed by anatomical closure of the foramen ovale due to fusion of the septum primum to the septum secundum.

Where anatomical closure of the foramen ovale does not occur, a PFO is created. Studies have shown that a relatively large percentage of adults have a PFO. The presence of a PFO is generally considered to have no therapeutic consequence in otherwise healthy adults. Because left atrial (LA) pressure is normally higher than right atrial (RA) pressure, the flap usually stays closed. Under certain conditions, however, right atrial pressure can exceed left atrial pressure, creating the possibility that blood could pass from the right atrium to the left atrium and blood clots could enter the systemic circulation. It is desirable that this circumstance be eliminated.

Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. It has been estimated that in 50% of cryptogenic strokes, a PFO is present. In addition, there is significant evidence that patients with a PFO who have had a cerebral vascular event are at increased risk for future, recurrent cerebrovascular events.

Patients suffering a cryptogenic stroke or a transient ischemic attack (TIA) in the presence of a PFO often are considered for medical therapy to reduce the risk of a recurrent embolic event. Accordingly, patients at such an increased risk are considered for prophylactic medical therapy to reduce the risk of a recurrent embolic event. These patients are commonly treated with oral anticoagulants to reduce the risk of a recurrent embolic event. However, these anticoagulants have potentially adverse side effects, including hemorrhaging, hematoma, and adverse interactions with other drugs. In addition, use of anticoagulant drugs can alter a person's recovery and necessitate adjustments in a person's daily living pattern.

Where anticoagulation is contraindicated, surgery may be employed to close a PFO. The surgery would typically include suturing a PFO closed by attaching septum secundum to septum primum. Like other open surgical treatments, however, this surgery is highly invasive, risky, requires general anesthesia, and may result in lengthy recuperation.

Nonsurgical closure of PFOs has become possible with the introduction various mechanical closure devices, including umbrella devices and the like, which were initially for percutaneous closure of atrial septal defects (ASDs; a condition where there is not a septum primum). These devices potentially allow patients to avoid the side effects often associated with anticoagulation therapies and the risks of invasive surgery.

However, devices for treating heart defects, such as PFO and other atrial and ventricular septal heart defects have their share of drawbacks. The complex anatomical features of PFOs present a challenge to a one size fits all approach. The PFO involves two components, septum primum and septum secundum. The septum secundum is thicker than septum primum and exhibits limited mobility and compliance. Failure of these two structures to fuse creates a tunnel-like opening, the PFO. The distance of the nonfusion between the two septa determines the particular size of the PFO, which must be considered in the design of a device targeting PFOs. Nevertheless, devices are often configured so that the patient's anatomy must be adjusted to fit the geometry of the device. As a consequence, heart tissue may be torn when accommodating such devices.

Conventional nonsurgical closure devices are often technically complex, bulky, have a high septal profile, low radiopacity, and an inability to provide immediate closure. Additionally, many of the devices have a geometry which tends to prevent the device from remaining flat against, or within the defect once deployed. The varying passageway geometries often require multiple sized devices. Moreover, many devices are set apart by a relatively long central section corresponding to the PFO tunnel. By increasing the device profile, the device can present difficulties with respect to complete endothelialization. Conventional closure devices are often difficult to deploy or reposition, often require replacement or repositioning, and require relatively large delivery catheters (for example, 9-10 French or more). In addition, the large masses of foreign material associated with the device may lead to unfavorable body adaptation to the device, including thromboses or other unfavorable reactions. Further drawbacks to nonsurgical closure devices include complications resulting from fractures of the components, conduction system disturbances, perforations of heart tissue, residual leaks, and inability to allow subsequent methods involving transeptal puncturing.

Accordingly, there is a need for improved low profile closure devices and simplified delivery methods for immediate closure, which are capable of limiting the amount of foreign material deployed and enhancing closure stability. The present invention is designed to address a number of the deficiencies surrounding conventional closure devices.

BRIEF SUMMARY OF THE INVENTION

In one embodiment, the present invention provides a closure device for closing a bodily passageway. The closure device includes a first frame, a second frame, a first crossbar, and a second crossbar. A sheet of biocompatible material is attached to the first frame. The first crossbar extends across the first frame. The first crossbar has terminal crossbar ends connectively linked to separate sites on the first frame. Likewise, the second crossbar extends across the second frame and has terminal crossbar ends connectively linked to separate sites on the second frame. The first and second crossbars are attached to each other at a connection point, and the first and second crossbars are each configured to bend away from the connection point when the closure device is deployed to close a bodily passageway.

In another embodiment, a closure device assembly is provided. The assembly includes a delivery catheter housing, a delivery release member, and a collapsibly disposed closure device, such as the closure device described above.

In yet another embodiment, a method for closing a bodily passageway in a patient is provided. The method includes providing a closure device assembly, including a delivery catheter housing, a delivery release member, and a closure device, such as the closure device described above. For example, the closure device includes a first and second frame, as described above. The method further includes advancing the delivery catheter housing through the bodily passageway and releasing the first frame from the delivery catheter housing proximate to a first opening of the bodily passageway. The method also includes retracting the delivery catheter housing through the bodily passageway, positioning the delivery catheter housing proximate to a second opening of the bodily passageway, and disengaging the closure device from the delivery release member to release the second frame of closure device proximate to the second opening of the bodily passageway. The closure device is secured to tissue portions surrounding the bodily passageway, thereby closing the bodily passageway.

In still another embodiment of the present invention, a method for making a closure device for closing a bodily passageway is provided. The method includes threading one or more first retention members through one or more first tubular members to create a first frame, and threading the first retention member(s) through a first crossbar and a third crossbar. The method further includes fastening the first retention member(s) to hold together the first tubular member(s), the first crossbar and the third crossbar. Similarly to the foregoing steps, the method includes threading one or more second retention members though one or more second tubular members to create a second frame, threading the second retention member(s) through a second crossbar and a fourth crossbar, and fastening the second retention member(s) to hold together the second tubular member(s), the second crossbar and the fourth crossbar. The method further includes attaching a central portion of the first crossbar to the second crossbar and attaching a central portion of the third crossbar to the fourth crossbar. In addition, the method includes threading one or more third retention members through a delivery bar and fastening the third retention member(s) to one or more of the following: the first tubular member(s), the second tubular member(s), the first retention member(s), or the second retention member(s).

Further aspects, features, and advantages of the invention will become apparent from consideration of the following description and the appended claims when taken in connection with the accompanying drawings.

DETAILED DESCRIPTION OF THE INVENTION

A closure device for closing or occluding bodily passageways, including septal openings of the heart is provided. As used herein, the terms "opening", "bodily opening", "passageway", and "bodily passageway" are interchangeably used to refer to a bodily opening, aperture, canal, conduit, or duct, including but not limited to septal openings, heart valves, blood vessels, vessel punctures, bile ducts, and the like. Unlike certain other PFO closure devices in the prior art, the closure device of the present invention can provide reduced foreign materials, a low profile, self-centering capacity, good radiopacity, simplified delivery, and an increased capacity for immediate closure of a variety of passageway sizes. Without wishing to be bound by a particular theory or to in any way limit the scope of the appended claims and their equivalents, it is believed that incorporation of bioremodelable material capable of causing angiogenesis and replacement by host tissues according to the present invention provides a more stable and permanent closure compared to conventional closure devices.

Figure 1:
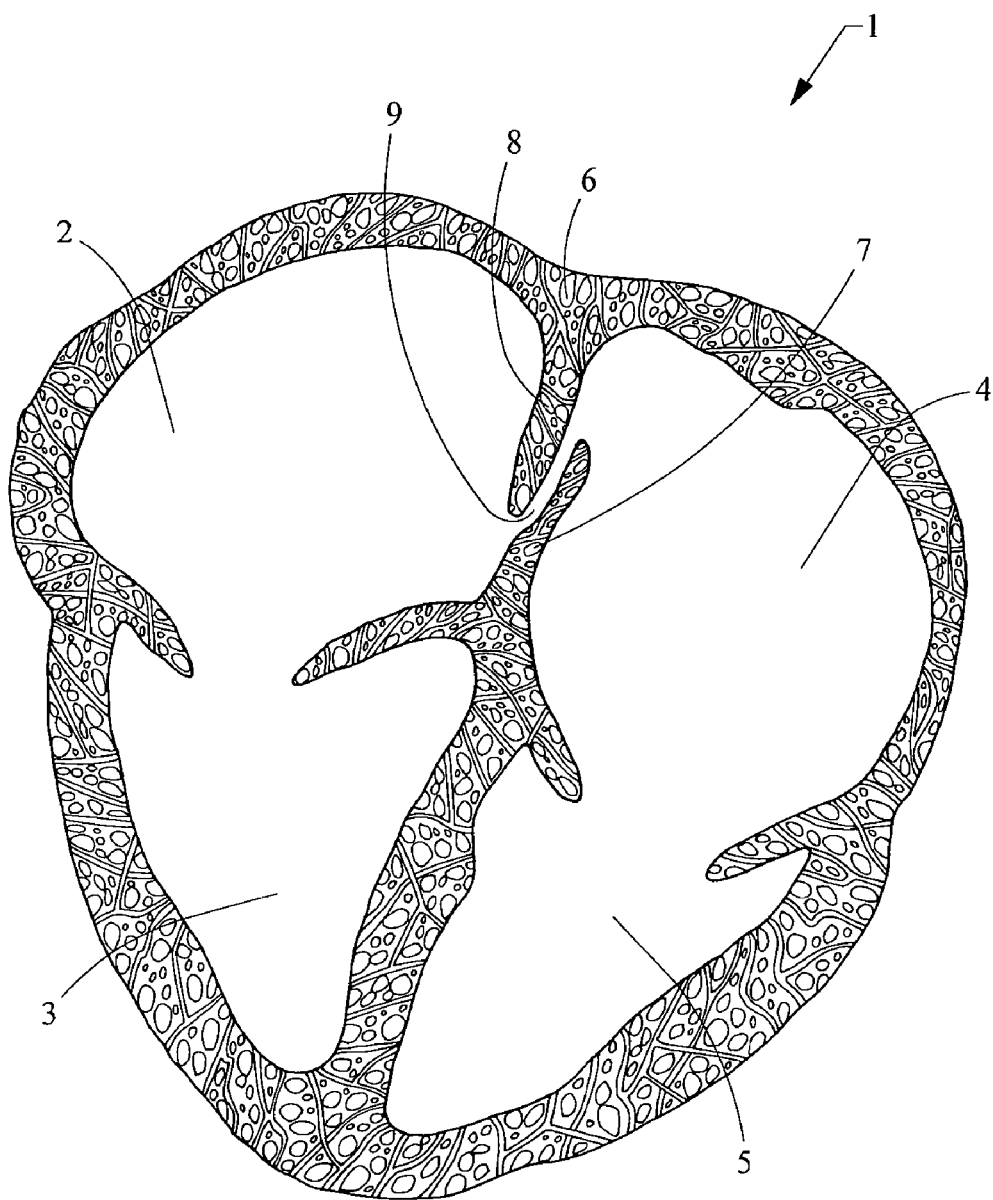
FIG. 1 is a cross-section view of a heart having a PFO.

FIG. 1 is a schematic front view of a heart 2 with a septal defect, such as patent foramen ovale (PFO). The heart 1 has a right atrium 2, right ventricle 3, left atrium 4, and a left ventricle 5. The septum 6 between the right atrium 2 and the left atrium 4 comprises a septum primum 7 and a septum secundum 8. The PFO 9 is an opening in the septum 6 that has not properly closed. Where a PFO 9 is present, the septum primum 7 typically overlaps the septum secundum 8 and the higher pressure in the left atrium 4 typically closes the flaps of the septum primum 7 and the septum secundum 8 so that blood does not leak between the atria 2 and 4. However, when there is a pressure change in the chest, the flaps may separate permitting blood to flow through the PFO and between the atria 2 and 4.

Figure 2:
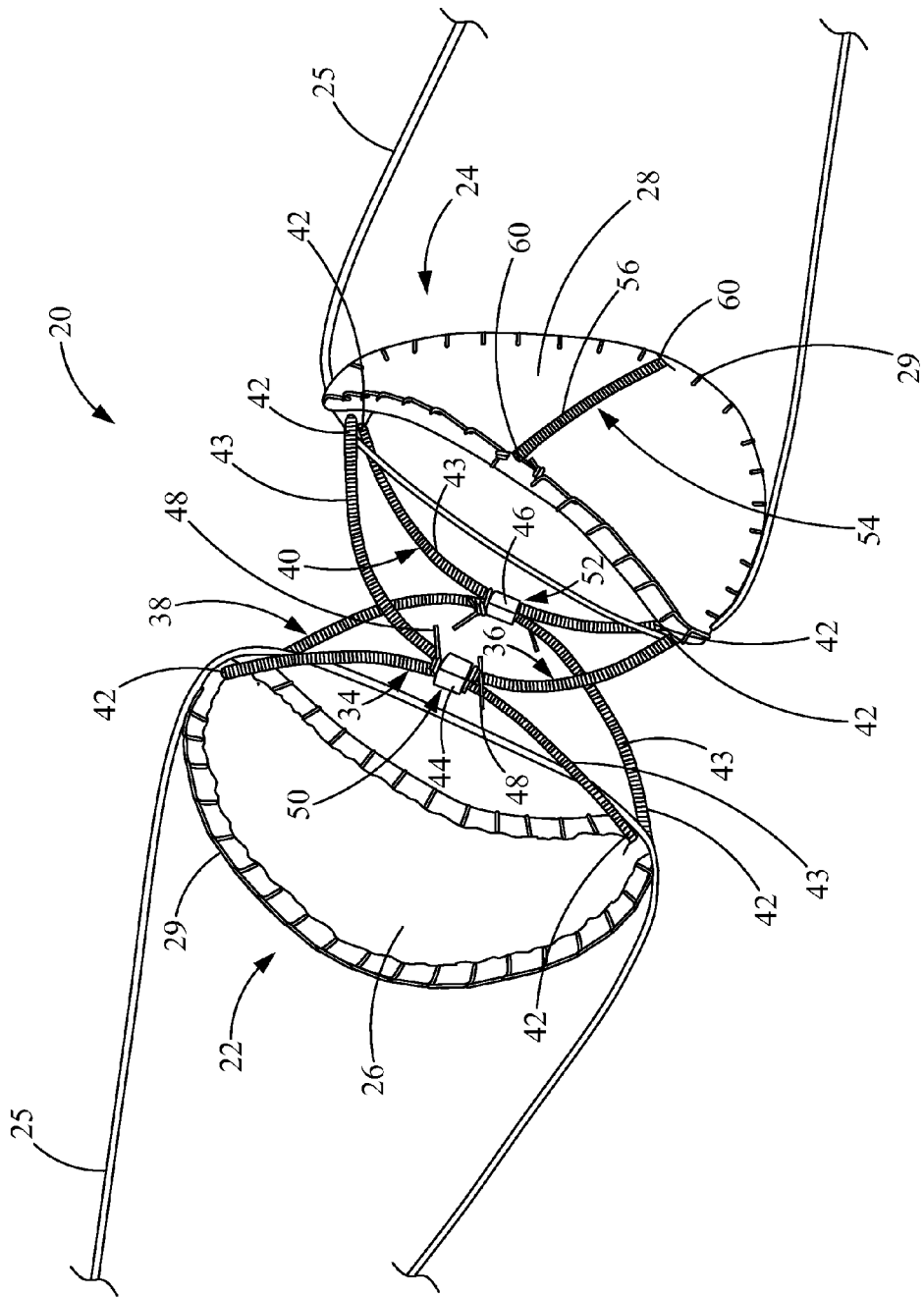
FIG. 2 is perspective view of an exemplary closure device according to an embodiment of the present invention.

Now referring to FIG. 2, closure device for closing a bodily passage is provided and generally indicated at reference numeral 20. The closure device 20 includes a first frame 22 and a second frame 24. The first and second frames 22, 24 may be generally circular, as shown, or elliptical, or having any other suitable shape, within the spirit and scope of the present invention. For example, the frames could have a polygonal shape. The frames 22, 24 may have straight or curved edges.

The frames 22, 24 may be in the form of a closed or substantially closed wire, coil, tubular structure, or bar-like structure. One or both of the frames 22, 24 may be discontinuous, provided that at least one of the frames 22, 24 is capable of supporting a sheet of biocompatible material onto a frame configuration suitable for covering a septal opening, such as a PFO. Exemplary polygonal shapes include, but are not limited to triangle, quadrilateral, square, pentagon, hexagon, octagon, and the like. Circular shapes include circle, oval, ellipse, and the like, by way of example.

Figure 3:
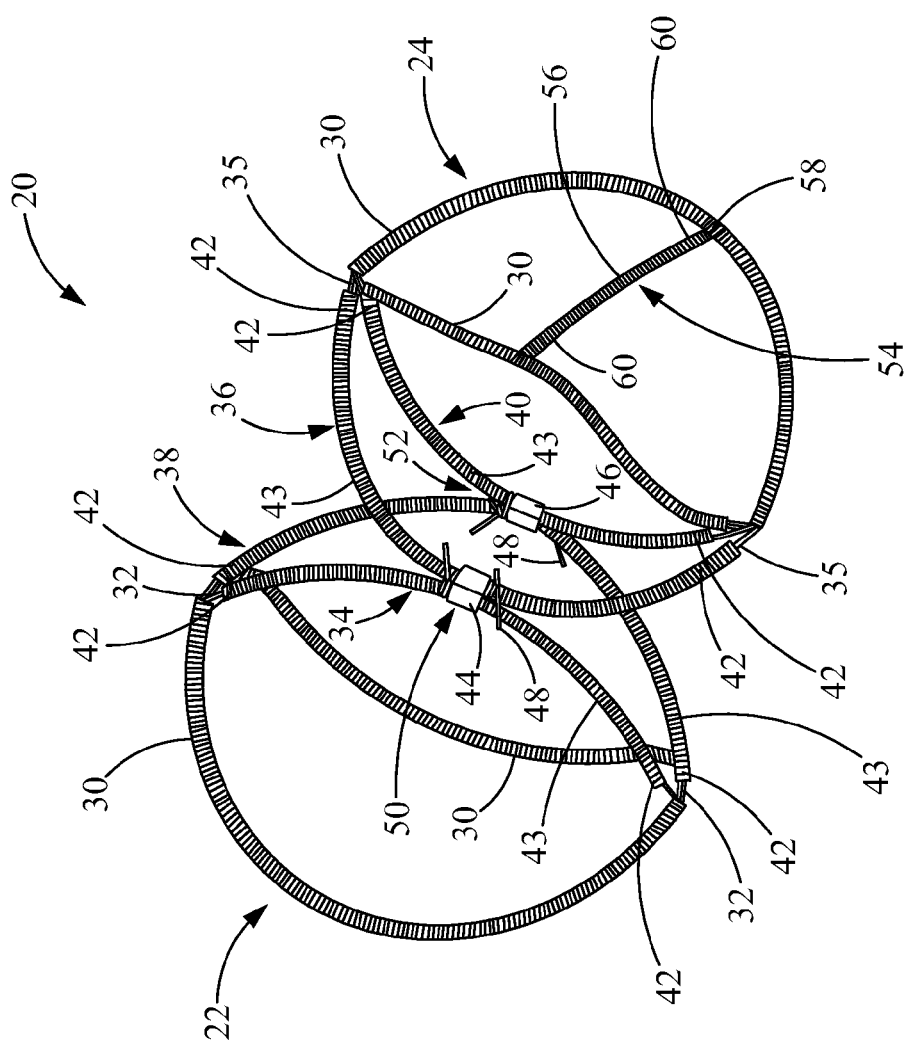
FIG. 3 is a perspective view of the closure device of FIG. 2, showing the closure device without biocompatible sheets to provide further details of the frames, in accordance with the principles of the present invention.

Generally, the frames 22, 24 have a first configuration wherein the sides and bends generally lie within a single, flat plane, and a second configuration whereby sides and bends are brought in closer proximity to one another when the frames 22, 24 are collapsibly disposed in a delivery catheter. Further, the frames 22, 24 of FIGS. 2 and 3 are shown pulled apart with cords 25, to better show the detail of the frames 22, 24. In the pulled-apart configuration, the frames 22, 24 may be bent and may not lie in a completely flat plane.

In one aspect, the frames 22, 24 are formed from one or more tubular members. The tubular members could be, for example, in the form of coils, bars, wires, or other hollow tubular members. The frames 22, 24 may be formed from a variety of wire or non-wire materials differing in shape and material substance. For example, the frames 22, 24 may be formed from flat or rounded wires having a variety of cross-sectional shapes (for example, oval, delta, D-, and the like). The frames 22, 24 may each be formed from a single tubular member or other material having a plurality of sides and bends each interconnecting adjacent sides, or they may each be formed from multiple tubular members. A closed circumferential frame 22, 24 may be formed a single piece of continuous, circumferential tube or coil, for example, or it may be joined by any suitable attachment mechanism, including, but not limited to cannula and solder, spot welding, and the like.

Additionally, the frames 22, 24 may be formed from one or more linked coils or laser cut from a tube or bar. Generally, the frames 22, 24 may be formed from metallic material, such as platinum, stainless steel or Nitinol. The tube or bar may be hollow or filled. Additional methods for forming or manipulating a circumferential frame are described in described in U.S. Patent Application Publication No. 2001/0039450 A1, the disclosures of which are expressly incorporated by reference herein.

When using frames 22, 24 that are formed from coils or hollow tubular members, wires, threaded materials, sutures, adhesives or metallic couplers may be used to join the coil or hollow tubular member ends. Alternatively, the ends may be directly joined to one another by soldering or welding. Alternatively, the frames 22, 24 may be prefabricated as a continuous closed structure, or as a non-continuous structure. The use of a coil in a frame 22, 24 can provide additional flexibility for repositioning or removal of the closure device 20 when using snares or other suitable removal or retrieval devices known to those of skill in the art.

The frame 22, 24 may be variably sized depending on the size of the bodily passageway or septal opening, such as a PFO. In particular, the frames 22, 24 are each configured to completely overlap the opening at one end of the bodily passageway. Accordingly, the frames 22, 24 may be configured with a diameter size or (diagonal size for polygonal frames) between about 5 mm and about 50 mm, preferably between about 10 mm and about 30 mm, or between about 15 mm and about 25 mm. By way of example, a frame 22, 24 having a diameter size (or diagonal size for polygonal frames) between about 18 and about 20 mm may be used for closing most PFOs, while a size between about 25 and about 30 mm may be used for closing PFOs and other septal defects. Accordingly, the frames 22, 24 may be configured with a diameter size ranging from about 15 to about 35 mm, preferably between about 18 to about 30 mm.

The first and second frames 22, 24 are each covered by a sheet of biocompatible material. For example a first sheet 26 of biocompatible material is attached to the first frame 22, and a second sheet 28 of biocompatible material is attached to the second frame 24. The frames 22, 24 may be partially or substantially covered by the sheets 26, 28 of biocompatible material. In some embodiments, however, one of the frames 22, 24 may not have a biocompatible material sheet covering it.

As used herein, the term "biocompatible" refers to a material that is substantially non-toxic in the in vivo environment of its intended use, and that is not substantially rejected by the patient's physiological system or is non-antigenic. This can be gauged by the ability of a material to pass the biocompatibility tests set forth in International Standards Organization (ISO) Standard No. 10993; the U.S. Pharmacopeia (USP) 23; or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, immunogenicity, and combinations thereof. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Bioremodelable materials, including collagenous ECM materials and intestinal submucosal tissue materials, provide a preferred source of biocompatible sheet 26, 28 materials for attachment to the frames 22, 24. The bioremodelable material used for the sheets 26, 28 may be configured to close a bodily passageway.

As used herein, the term "bioremodelable" refers to a natural or synthetic material that is bioresorbable and capable of inducing angiogenesis, tissue remodeling, or both in a subject or host. "Angiogenesis" and "angiogenic" refer to bioactive properties, which may be conferred by a bioremodelable material through the presence of growth factors and the like, which are defined by formation of capillaries or microvessels from existing vasculature in a process necessary for tissue growth, where the microvessels provide transport of oxygen and nutrients to the developing tissues and remove waste products. "Bioresorbable" refers to those materials of either synthetic or natural origin which, when placed in a living body, are degraded through either enzymatic, hydrolytic or other chemical reactions or cellular processes into by-products which are either integrated into, or expelled from, the body. It is recognized that in the literature, the terms "resorbable", "absorbable", and "bioabsorbable" are frequently used interchangeably.

A bioremodelable material includes at least one bioactive agent capable of inducing angiogenesis or tissue remodeling. One or more bioactive agents in the bioremodelable material may stimulate infiltration of native cells into an acellular matrix, and formation of new blood vessels (capillaries) growing into the matrix to nourish the infiltrating cells (angiogenesis). Additionally, the bioactive agents may cause the degradation or replacement of the bioremodelable material by endogenous tissue. The bioremodelable material may include a naturally derived collagenous ECM tissue structure present in, for example, native submucosal tissue sources, including, but not limited to small intestine submucosal (SIS) tissue, or it may include any one of a variety of different non-submucosal ECM-containing tissue materials or synthetic, bioresorbable non-ECM materials capable of inducing angiogenesis and tissue remodeling in a host.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers, such the lamina muscularis mucosa and the stratum compactum. A submucosal material may be a decellularized or acellular tissue, which means it is devoid of intact viable cells, although some cell components may remain in the tissue following purification from a natural source. Alternative embodiments (for example, fluidized compositions and the like) include submucosal material expressly derived from a purified submucosal matrix structure. Submucosal materials according to the present disclosure are distinguished from collagen materials in other closure devices that do not retain their native submucosal structures or that were not prepared from purified submucosal starting materials first removed from a natural submucosal tissue source.

The term "small intestinal submucosa" (SIS) refers to a particular submucosal tissue structure removed from a small intestine source, such as pig.

The "sheet of biocompatible material" and "sheet of bioremodelable material" refer to one or more biocompatible or bioremodelable tissue layers or synthetic polymeric layers formed into a sheet or composite thereof. A sheet of biocompatible or bioremodelable material may include, for example, one or more naturally-derived tissue layers containing an ECM scaffold, one or more biocompatible polymeric layers, or combinations thereof. The sheet of biocompatible or bioremodelable material can be in the form of a single tissue or polymeric layer or a plurality of tissue or polymeric layers in form of laminates, composites, or combinations thereof. Preferred bioremodelable materials include naturally derived tissues with ECMs possessing biotropic properties, including in certain forms angiogenic collagenous ECMs. Preferred ECMs includes naturally-derived collagenous tissue material retaining native matrix configurations and bioactive agents, such as growth factors, which serve to facilitate tissue remodeling. In the alternative, collagen-based materials formed by separately purifying natural collagen and other associated components away from their native three dimensional matrix configurations or bioactive agents, including growth factors, may be used. Suitable collagenous ECMs include those derived from a variety of native tissues, including but not limited to, intestine, stomach, bladder, liver, fascia, skin, artery, vein, pericardium, pleura, heart valve, dura mater, ligament, tendon, bone, cartilage, bladder, liver, including submucosal tissues therefrom, renal capsule membrane, dermal collagen, serosa, mesenterium, peritoneum, mesothelium, various tissue membranes and basement membrane layers, including liver basement membrane, and the like. Suitable submucosa tissue materials for these purposes include, for instance, intestinal submucosa, including small intestinal submucosa, stomach submucosa, urinary bladder submucosa, and uterine submucosa. A particularly preferred ECM material is porcine SIS material. Commercially available ECM materials capable of remodeling to the qualities of its host when implanted in human soft tissues include porcine SIS material (Surgisi$^{SM}$ and Oasi$^{SM}$ lines of SIS materials, Cook Biotech Inc., West Lafayette, Ind.) and bovine pericardium (Peri-Strip$^{SM}$, Synovis Surgical Innovations, St. Paul, Minn.).

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), platelet derived growth factor (PDGF), and other growth factors known to those of skill in the art. As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein expression, gene expression, or combinations thereof.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example, at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material (C. Heeschen et al., Nature Medicine 7 (2001), No. 7, 833-839). When combined with a fluorescence microangiography technique, this model can provide both quantitative and qualitative measures of angiogenesis into biomaterials (C. Johnson et al., Circulation Research 94 (2004), No. 2, 262-268).

In addition to, or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (for example, human proteins applied to collagenous ECMs from other animals, such as pigs). The non-native bioactive components may also be drug substances. Illustrative drug substances that may be incorporated into or onto the ECM materials used in the invention include, for example, antibiotics or thrombus-promoting substances such as blood clotting factors, for example, thrombin, fibrinogen, and the like. These substances may be applied to the ECM material as a premanufactured step, immediately prior to the procedure (for example, by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al., which is incorporated by reference herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

A preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants and better preserves the aseptic state and inherent biochemical form of the submucosa, thereby potentiating its beneficial effects. Alternatively, the ECM- or submucosa may be purified a process in which the sterilization step is carried out after delamination as described in U.S. Pat. Nos. 5,993,844 and 6,572,650.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example, by chemical treatment, the matrix structure may be wrapped in a plastic or foil wrap and sterilized again using electron beam or gamma irradiation sterilization techniques.

Bioremodelable materials, including ECMs according to the present invention, may be isolated and used in the form of intact natural sheets, tissue layers, or strips, which may be optimally configured from a native, wet, fluidized, or dry formulation or states, into sheets, knitted meshes, or porous scaffolds, using one or more of the following, including stretching, chemical crosslinking, lamination under dehydrating conditions, compression under dehydrating conditions, in accordance with teachings set forth in U.S. Pat. Nos. 6,206,931 and 6,358,284; U.S. Patent Application Publication Nos. 2006/0201996, 2006/0052816, 2005/0249772, and 2004/0166169, the disclosures of which are expressly incorporated by reference herein.

In addition, bioremodelable materials according to the present invention may be treated by controlled autolysis to render the materials substantially acellular and less susceptible to post-implantation mineralization as described in U.S. Pat. Nos. 5,595,571, 5,720,777, 5,843,180, 5,843,181, and U.S. Patent Application Publication Nos. 2005/020612, the disclosures of which are expressly incorporated by reference herein.

The bioremodelable material as used herein may be designed to promote angiogenesis and endothelialization of the implanted closure device 20. In particular, the bioremodelable material may be provided to be capable of remodeling the surrounding tissues, such that upon implantation, in a patient, the sheet of bioremodelable material is degraded and replaced by the patient's endogenous tissues. As the sheet of bioremodelable material is remodeled by host tissues, the bodily opening becomes stably closed, obviating concerns about migration of the device.

Bioremodelable sheet materials provide a preferred source of biocompatible sheet materials for attachment to the frame. However, other biocompatible sheet materials may be used in place of bioremodelable sheet material, including composites thereof. Biocompatible sheet materials include a variety of natural or synthetic polymeric material known to those of skill in the art which can be formed into a flexible sheet material covering the above described frames 22, 24. Exemplary biocompatible sheet materials include polymeric materials; fibrous materials; thrombogenic fibrous materials, and other materials known to those of skill in the art.

Biocompatible sheet materials may be formed from fibers, or any suitable material (natural, synthetic, or combination thereof) that is pliable, strong, resilient, elastic, and flexible. The material should be biocompatible or capable of being rendered biocompatible by coating, chemical treatment, or the like. Thus, in general, the material may comprise a synthetic biocompatible material that may include, for example, bioresorbable materials such as polylactic acid (PLA), polyglycolic acid (PGA), polycaprolactone (PCL), polydioxanone (PDO), trimethylene carbonate (TMC), polyvinyl alcohol (PVA), and copolymers or blends thereof; polyurethanes, including THORALON™ (THORATEC, Pleasanton, Calif.), as described in U.S. Pat. Nos. 4,675,361, 6,939,377, and U.S. Patent Application Publication No. 2006/0052816, the disclosures of which are incorporated by reference herein; cellulose acetate, cellulose nitrate, silicone, polyethylene terephthalate, polyamide, polyester, polyorthoester, polyanhydride, polyether sulfone, polycarbonate, polypropylene, high molecular weight polyethylene, polytetrafluoroethylene, or mixtures or copolymers thereof, a polyanhydride, polycaprolactone, polyhydroxy-butyrate valerate, polyhydroxyalkanoate, or another polymer able to be made biocompatible.

Thrombogenic fibrous materials include synthetic or natural fibrous material having thrombogenic properties. Exemplary thrombogenic fibrous materials include, but are not limited to, DACRON, cotton, silk, wool, polyester thread and the like.

The polymeric materials may include a textile material. The textile includes fibers and may take many forms, including woven (including knitted) and non-woven. Preferably, the fibers of the textile comprise a synthetic polymer. Preferred textiles include those formed from polyethylene terephthalate, polytetrafluoroethylene (PTFE), and expanded polytetrafluoroethylene (ePTFE). These materials are inexpensive, easy to handle, have good physical characteristics and are suitable for clinical application. These materials may be attached to or rolled around a hollow tube or coil as described above.

Examples of biocompatible materials from which textiles can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile material, provided the final textile is biocompatible. Polymeric materials that can be formed into fibers suitable for making textiles include polyethylene, polypropylene, polyaramids, polyacrylonitrile, nylons and cellulose, in addition to polyesters, fluorinated polymers, and polyurethanes as listed above. Preferably the textile is made of one or more polymers that do not require treatment or modification to be biocompatible. More preferably, the textile is made of a biocompatible polyester. Examples of biocompatible polyesters include DACRON (DUPONT, Wilmington, Del.) and TWILLWEAVE MICREL (VASCUTEK, Renfrewshire, Scotland).

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver, disclosure of which is incorporated by reference. Fibers similar to those described are currently being manufactured by the DuPont Company from polyethylene terephthalate (often known as "DACRON" when manufactured by DuPont), and by other companies from various substances.

Non-native bioactive components, such as those synthetically produced by recombinant technology or other methods, may be incorporated into these other biocompatible materials. These non-native bioactive components may be naturally-derived or recombinantly produced proteins, such as growth factors, which are normally found in ECM tissues. These proteins may be obtained from or engineered from any animal species. The non-native bioactive components may also be drug substances. Illustrative drug substances that may be incorporated into or onto the ECM materials used in the invention include, for example, antibiotics or thrombus-promoting substances such as blood clotting factors, for example, thrombin, fibrinogen, and the like. These substances may be applied to the biocompatible material as a premanufactured step, immediately prior to the procedure (for example, by soaking the material in a solution containing a suitable antibiotic such as cefazolin), or during or after engraftment of the material in the patient.

ECM sheet materials or bioremodelable sheet materials formed from one or more layers of intestinal submucosal tissue are particularly preferred sources of bioremodelable materials for covering the frames 22, 24. However, other biocompatible sheet 26, 28 materials may be used in place of bioremodelable sheet material, including composites thereof. Exemplary biocompatible sheet materials include natural or synthetic polymeric or fibrous sheet materials, including DACRON, polytetrafluoroethylene (PTFE), expanded polytetrafluoroethylene (ePTFE), cotton, silk, wool, polyester, combinations thereof, and the like, which are further described below.

The sheets 26, 28 of material may include a flexible, pliable material configured onto the frames 22, 24 to project into a passageway, substantially conforming to one or more portions defining the passageway. The sheets 26, 28 may be sized or pre-stretched in accordance with a variety of desired three dimensional conformations, shapes, depths, and sizes suitable for closing or occluding a bodily passageway. The sheets 26, 28 may be laid flat over the frames 22, 24, or they may have a contoured shape, such as a dome shape. For example, the sheets 26, 28 of material may be applied to each of the frames 22, 24 whereby the cross-sectional area of the sheets 26, 28 are greater than the cross-sectional areas of the frames 22, 24. Thus, the sheets 26, 28 of material may be configured to take on a three dimensional conformation when deployed. Depending on the configuration of its attachment to elements of the closure device 20, the sheets 26, 28 of biocompatible material can adapt to a variety of bodily passageway shapes and sizes.

The sheets 26, 28 of biocompatible or bioremodelable material may be attached to the frames 22, 24 by any suitable attachment method. For example, the sheets 26, 28 of biocompatible of bioremodelable material may be attached by sutures 29. Alternative attachment methods include, but are not limited to, use of biological adhesives, use of chemical cross-linking agents, crimping, tissue welding, heat welding, pressure welding, heat source, light source, radiofrequency, lasering, other energy sources, and the like. Methods for attaching sheet materials to frames are described in U.S. Patent Application Publication No. 2001/0039450 A1, the disclosures of which are expressly incorporated by reference herein.

In the embodiment of FIG. 2, the sheets 26, 28 of biocompatible material are folded over the frames 22, 24 to substantially cover the frames 22, 24, and sutures 29 are used to sew the biocompatible sheets 26, 28 around the periphery of the frames 22, 24.

FIG. 3 illustrates the closure device 20 of FIG. 2 without the sheets 26, 28 of biocompatible material and without the cords 25, in order to show the frames 22, 24 in more detail. Each frame 22, 24 comprises two coils 30. Together, the coils 30 form a closed ring, each frame coil 30 defining a hemispheric coil ring portion. The coils 30 are hollow tubes having retention members 32, 35 such as wires, disposed therein, which will be described in further detail below. The retention members 32, 35 extend through the lumens of the coils 30 of the first and second frames 22, 24 and connect crossbars 34, 36, 38, 40 to the frames 22, 24. In this embodiment, a first retention member 32 extends through the lumens of the coils 30 of the first frame 22 and the lumens of the coils 43 of the first crossbar 34 and the third crossbar 38; and a second retention member 35 extends through the lumens of the coils 30 of the second frame 24 and the lumens of the coils 43 of the second crossbar 36 and the fourth crossbar 40.

For example, a first crossbar 34 extends across the first frame 22 and has terminal ends 42 connectively linked to separate sites on the first frame 22. "Connectively linked" and "connectively linking" interchangeably refer to the joining, adhering, bonding, attaching, or the like. In other words, the terminal ends 42 are connected to discontinuous sites on the circumference of the first frame 22. In this embodiment, the terminal ends 42 of the first crossbar 34 are connectively linked to opposite sides of the first frame 22. Likewise, a second crossbar 36 extends across the second frame 24 and has terminal ends 42 connectively linked to separate sites on the second frame 24, similarly to the configuration of the first crossbar 34 and the first frame 22.

The first and second crossbars 34, 36 are attached to each other via a coupling member 44. In one embodiment, the coupling member 44 is formed from a small hollow cannula or band co-encircling the first and second crossbars 34, 36, which may be a marker band having radiopaque properties, although the radiopaque properties are optional for the present invention. The coupling member 44 may be formed from any material suitable for coupling or joining the crossbars 34, 36. The coupling member 44 is preferably formed from a metallic material suitable for joining device components of the present invention, including but not limited to platinum, stainless steel, or Nitinol.

In this embodiment, the coupling member 44 is a marker band, but the coupling member 44 could alternatively or additionally include a suture, or a wire, for example, or any other suitable coupling device. Further, the first and second crossbars 34, 36 could also or alternatively be joined together, by welding, soldering, or an adhesive, by way of example.

In the present embodiment, a third crossbar 38 also extends across the first frame 22 and has terminal ends 42 connectively linked to separate sites on the first frame 22. For example, each terminal end 42 of the third crossbar 38 is located on an opposite side of the first frame 22. A fourth crossbar 40 extends across the second frame 24, similarly to the configuration of the rest of the crossbars 34, 36, 38, and has terminal ends 42 connectively linked to separate sites on the second frame 24. The third and fourth crossbars 38, 40 are attached to each other via a coupling member 46, which may be similar to the coupling member 44 attaching the first and second crossbars 34, 36. Like the first and second crossbars 34, 36, the third and fourth crossbars 38, 40 may be attached additionally or alternatively in any suitable manner, such as the ways described above for the first and second crossbars 34, 36.

In FIGS. 2 and 3, sutures 48 surround the coupling members 44, 46, which aid in coupling the crossbars 34, 36, 38, 40, and aid in keeping the coupling members 44, 46 fairly centralized on the crossbars 34, 36, 38, 40. Therefore, a central portion of the first crossbar 34 is attached to a central portion of the second crossbar 36; and a central portion of the third crossbar 38 is attached to a central portion of the fourth crossbar 40. In this embodiment, the "central portion" of a crossbar refers to a position not more than 30% away from a geometric center of the crossbar.

The first and second crossbars 34, 36 are attached to each other at a first connection point 50. The first and second crossbars 34, 36 are each configured to bend away from the first connection point 50 when the closure device 20 is deployed in a bodily passageway. Likewise, the third and fourth crossbars 38, 40 are attached to each other at a second connection point 52. The third and fourth crossbars 38, 40 are each configured to bend away from the second connection point 52 when the closure device 20 is deployed in a bodily passageway.

FIGS. 2 and 3 exemplify closure devices 20 having a plurality of connected coils (or tubular members) 30 connected by one or more retention members or wires 32, 35. Any one of the first and second frames 22, 24, frame coils 30, crossbars 34, 36, 38, 40, crossbar coils 43, or hollow tubular members thereof may be independently linked to one or more wires or retention members, or they may be interlinked to other device components by one or more wires or loop structures in one or more additional steps.

Accordingly, as shown in the embodiment depicted in FIGS. 2 and 3, a closure device 20 may include two crossbar coils 43 connected to two frame coils 30 by wires 32 or 35. Use of any of the above described attachment means may be employed to directly or indirectly connect a frame 22, 24 to the crossbars 34, 36, 38, 40.

To facilitate the joining of one or more crossbar coils 43 to any one of the frame coils 30, or to facilitate the joining of the frames 22, 24 to the sheets 26, 28 of biocompatible or bioremodelable material, any one of the various coiled structures may be partially stretched to create interrupted regions or open grooves to facilitate linkage between coils and/or biocompatible materials using for example, wires 32, 35 or sutures 29. For example, open area crossbar coil 43 grooves may facilitate linkages between the first and second crossbars 34, 36 or between the third and fourth crossbars 38, 40 by providing open area connections to facilitate wire exchanges between the crossbar coil 43 grooves. Open area coil grooves may also provide open area connections facilitating suture exchanges between a frame coil 30 and a sheet 26, 28 of biocompatible material.

In addition to being attached to one or more of the frames 22, 24, the sheets 26, 28 of biocompatible material may be additionally attached along a portion of one or more of the crossbars 34, 36, 38, 40 or along the length of one or more of the crossbars in their entireties. Alternatively, the sheets 26, 28 of biocompatible material may be attached to one or both of the first and second frames 22, 24 only.

In some embodiments, a single wire 32 may be used to link the first frame 22, the first crossbar 34, and the third crossbar 38. More particularly, a single wire 32 may be threaded through the lumens of the linear frame coils 30 of the first frame 22 to circularize the first frame 22. The single wire 32 may be further threaded through the linear crossbar coil 43 of the first crossbar 34 and the linear crossbar coil 43 of the third crossbar 38, to connectively link the circularized frame coil 30 of the first frame 22 to the crossbar coils 43 of the first and third crossbars 34, 38.

For example, a single wire 32 may be run through the frame coil 30 (or hollow, tubular frame member) of the first frame 22 one or more times, at which point free wire ends at opposite ends of the first frame 22 are run toward each other, through the crossbar coils 43 in opposite directions. The ends of the wire 32 may then be extended through the crossbar coils 43 toward opposite ends in each case, and looped back into the other of the first and third crossbar coils 43, whereby the excess free ends can be clipped and crimped, tied, or further stabilized as necessary.

Alternative wiring configurations for linking the first frame 22 and the first and third crossbars 34, 38 may be employed. Moreover, wire ends may be completely extended through the crossbar coils 43 and looped around the first frame 22 before their exchange into the crossbar coils 43 a second time. It should be understood that the second frame 24, the second crossbar 36, and the fourth crossbar 40 may be connected similarly to the first frame 22, the first crossbar 34, and the third crossbar 38, as described above, with the use of the single wire 35, for example. In addition, further details regarding assembling the closure device are provided below.

Figure 4:
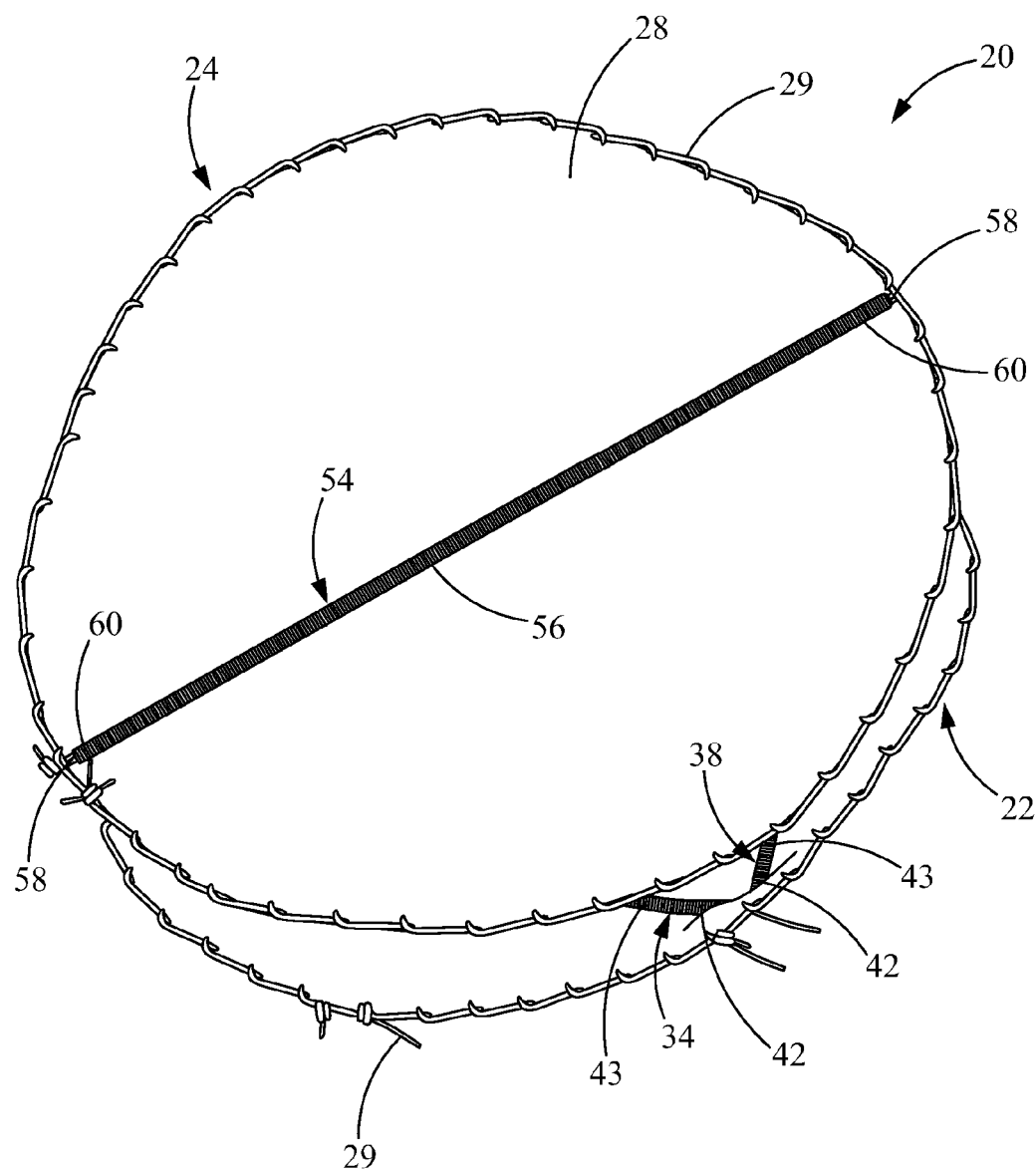
FIG. 4 is a right end perspective view of the closure device of FIGS. 2 and 3, according to the principles of the present invention.
Figure 5:
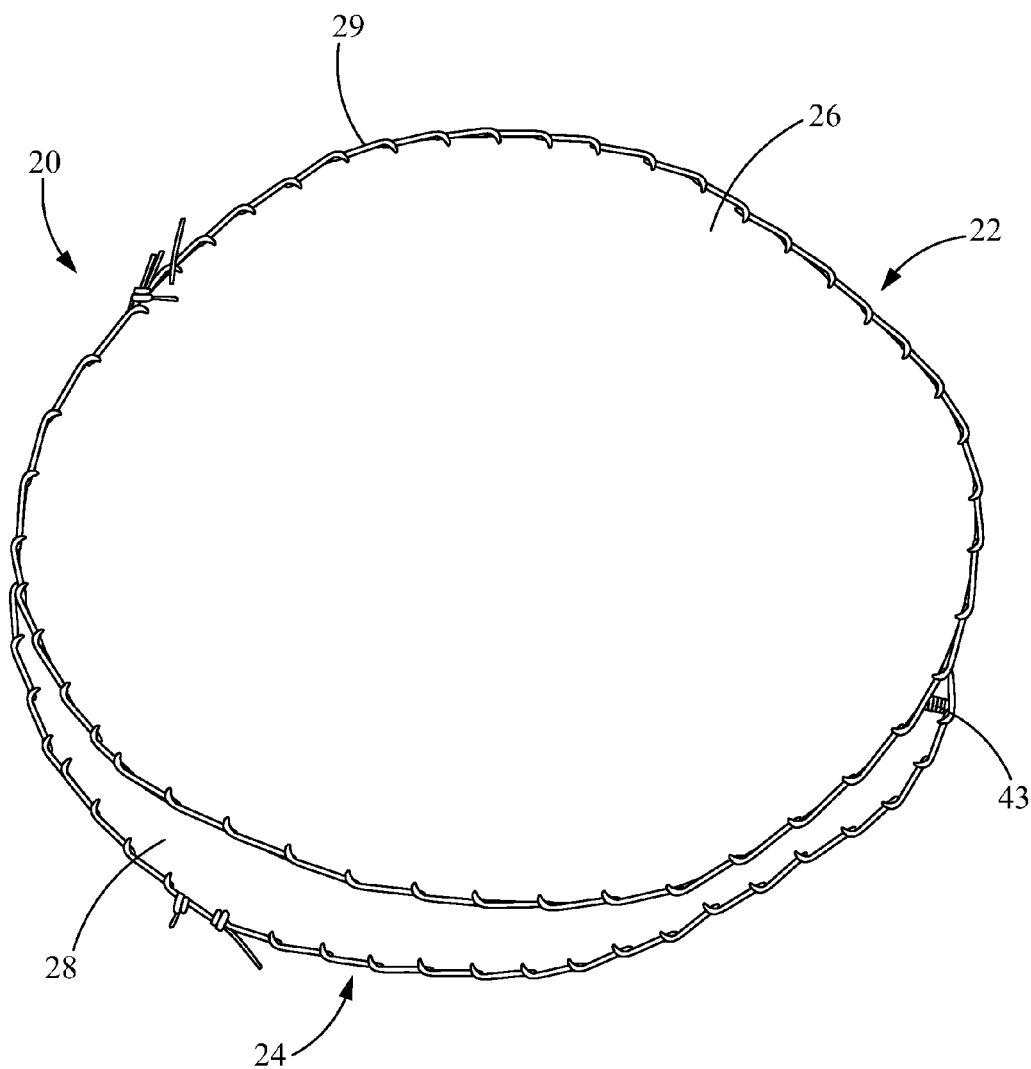
FIG. 5 is a left end perspective view of the closure device of FIGS. 2-4, in accordance with the principles of the present invention.
Figure 7:
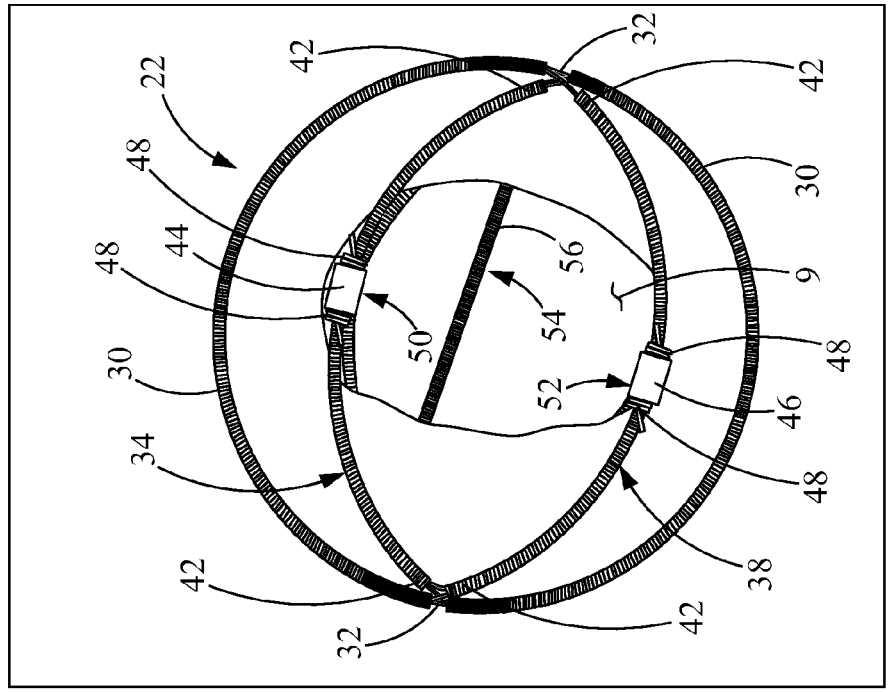
FIG. 7 is a left end view of the closure device of FIGS. 2-6 deployed in a bodily passageway, having both sheets of biocompatible material removed to show details of the frame and crossbar structures, in accordance with the principles of the present invention.
Figure 6:
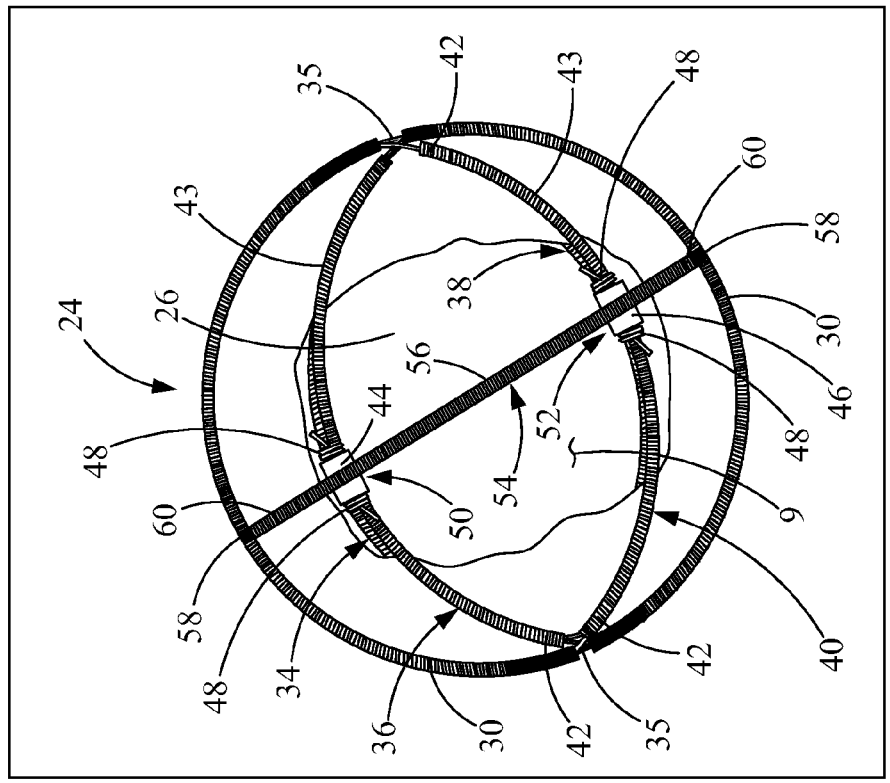
FIG. 6 is a right end view of the closure device of FIGS. 2-5 deployed in a bodily passageway, having one sheet of biocompatible material removed to show details of the frame and crossbar structures, according to the principles of the present invention.
Figure 8:
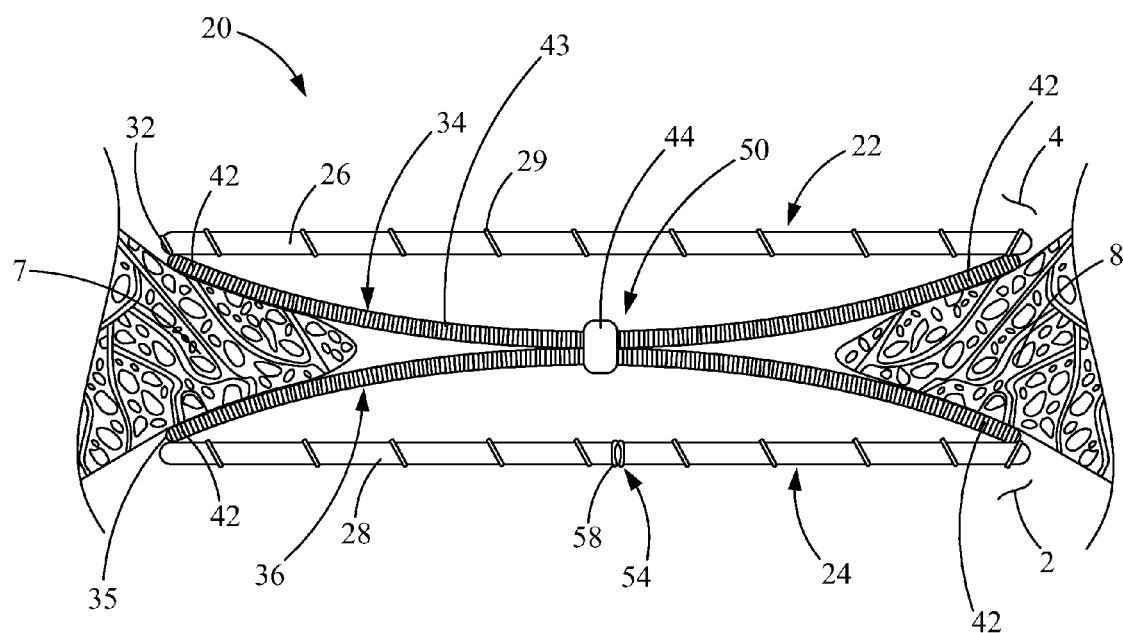
FIG. 8 is a side view of the closure device of FIGS. 2-7 deployed in a bodily passageway, according to the principles of the present invention.

Now referring to FIGS. 4 and 5, the closure device 20 is illustrated in a flatter configuration, without being pulled apart by the cords 25 shown in FIG. 2. Each of the first and second frames 22, 24 define a plane which is at least partially covered by the sheets 26, 28 of biocompatible material. Preferably the frames 22, 24 are substantially covered or completely covered by the sheets 26, 28 of biocompatible material. The sheets 26, 28 of biocompatible material provide a covering over the frames 22, 24, which is designed to cover or occlude a bodily passageway.

When deployed (see FIGS. 2-3, e.g.), the first and second crossbars 34, 36 are connected by the coupling member 44 at the first connection point 50. As described above, each of the first and second crossbars 34, 36 are configured to bend away from the first connection point 50. As such, the first crossbar 34 is configured to extend in an arc concave to the first frame 22 plane when deployed, and the second crossbar 36 is configured to extend in an arc convex to the first frame 22 plane when deployed. Accordingly, the second crossbar 36 is configured to extend in an arc concave to the second frame 24 plane when deployed, and the first crossbar 34 is configured to extend in an arc convex to the second frame 24 plane when deployed.

The third and fourth crossbars 38, 40 are configured similarly to the first and second crossbars 34, 36. Thus, the third and fourth crossbars 38, 40 are connected by the coupling member 46 at the second connection point 52, and each of the third and fourth crossbars 38, 40 are configured to bend away from the second connection point 52 when deployed. As such, the third crossbar 38 is configured to extend in an arc concave to the first frame 22 plane when deployed, and the fourth crossbar 40 is configured to extend in an arc convex to the first frame 22 plane when deployed. Conversely, the fourth crossbar 40 is configured to extend in an arc concave to the second frame 24 plane when deployed, and the third crossbar 38 is configured to extend in an arc convex to the second frame 24 plane when deployed.

Referring to FIGS. 2 and 3, the closure device 20 may additionally include a delivery bar 54 to enhance delivery or retrieval of the closure device 20. The delivery bar 54 may have a flexible, substantially linear structure configured for releasable attachment to a delivery release member. In the event that the closure device 20 is found to be not properly positioned, anchorage of the delivery bar 54 to a delivery release member permits the closure device 20 to be withdrawn and/or repositioned as necessary.

The delivery bar 54 may be comprised of a hollow tubular member, such as a coil or other hollow tube, or it may include merely a wire or other suitable member. In FIGS. 2 and 3, the delivery bar 54 is shown having a hollow coil 56, similar to the crossbar coils 43 and the frame coils 30. The delivery bar 54 has a retention member 58, such as a wire, disposed within the coil 56 and linked to the second frame 24; however, it should be understood that the delivery bar 54 could alternatively be linked to the first frame 22 or one of the crossbars 34, 36, 38, 40. The delivery bar has terminal delivery bar ends 60 that are connectively linked to the second frame 24 at discontinuous sites thereon; in other words, the terminal deliver bar ends 60 are connectively linked to separate sites on the second frame 24. The terminal delivery bar ends 60 may also be spaced apart from the terminal crossbar ends 42 of the second and fourth crossbars 36, 40. The terminal ends 60 may form loops to surround the wire 35 and/or the coil 30 of the second frame 24. For example, the retention members 58 may include loops extending therefrom and surrounding the second frame 24 to link the delivery bar 54 to the second frame 24.

In one aspect, the delivery bar 54 may include one or more grasping members (not shown) having a grasping structure or shape suitable (for example, loop, knob, ball, hook, and the like) for releasable attachment to a delivery release member facilitating delivery of the closure device 20. However, in other embodiments, a delivery release member may attach to the coil 56 or retention member 58 of the delivery bar 54 for deployment to close a bodily passageway. One or more delivery bars 54 may be used, or none may be used. In some embodiments, the delivery bar 54 may be connected to the sheet 28 of biocompatible or bioremodelable material using any suitable method of attachment.

The delivery bar 54 may be attached to the second frame 24 using sutures, clips, wires, staples, adhesives, crimping, tying, combinations thereof, or any other suitable attachment materials or attachment structures known to those of skill in the art.

The crossbars 34, 36, 38, 40 and the delivery bar 54 may be formed as flexible, substantially linear structures that may be configured from, or configured to include, a substantially one-dimensional tube, coil, bar, cannula, or wire having a circular, elliptical or polygonal cross-sectional shape. A crossbar 34, 36, 38, 40 or delivery bar 54 is preferably hollow in nature. This can facilitate linkage to other device components using retention members 32, 35, 58, such as wires, for example. It should be noted, however, that any materials providing flexibility and interconnectivity can be used for the crossbars 34, 36, 38, 40, delivery bar 54, and frame coils 30, including shape memory materials, braided wires and the like.

In the closure devices 20 of the present invention, one or more wires 32, 35, 58 may be used for interconnecting the frames 22, 24, crossbars 34, 36, 38, 40, and/or delivery bar 54. In addition to wires 32, 35, 58 and coupling members 44, 46, the above described structural components may be connected to one another using any suitable attachment means known to those of skill in the art, including but not limited to the sutures, adhesives, soldering, welding, crimping, and the like.

A closure device 20 of the present invention may be made of flexible materials so that the closure device is sufficiently collapsible to be retained and delivered from a variety of catheter delivery sizes, including 6-15 French size, preferably 8-12 French size. Accordingly, one or more of the component device parts of the closure device 20 may be made from flexible, radiopaque, materials such as platinum and/or or shape memory alloy materials, such as Nitinol, including those described in U.S. Pat. Nos. 4,665,906, 5,108,420, the disclosures of which are incorporated by reference herein.

Shape-memory materials may be included in a number of component closure device 20 parts, including, but not limited to the frame coils 30, the crossbar coils 43, the delivery bar coil 56, and the retention members 32, 35, 58. The shape-memory materials, including Nitinol alloys, may be utilized whereby the alloy materials are compressed or partially expanded in their martensitic state and fully expanded in their austenitic state. A specific shape memory alloy may be chosen so that the frames 22, 24 and the crossbars 34, 36, 38, 40 are in the austenitic state at body temperature. Prior to insertion into the body, the closure device 20 may be maintained at a low temperature within the martensitic range. Upon delivery to a desired bodily location, the closure device 20 may be warmed to at least the $A_f$ temperature so that it can expand to its desired configuration.

Suitable shape-memory materials and their use in medical applications is disclosed in U.S. Pat. No. 3,012,882 to Muldawer et al.; U.S. Pat. No. 3,174,851 to Buechler et al.; U.S. Pat. No. 4,665,906 to Jervis; U.S. Pat. No. 5,108,420 to Marks; U.S. Pat. No. 5,769,796 to Palermo et al., U.S. Pat. No. 5,846,247 to Unsworth et al.; and U.S. Pat. No. 6,451,052 to Burmeister et al., the disclosures of which are expressly incorporated herein by reference.

Preferably, the frames 22, 24 are made from, or at least include, flexible radiopaque materials, and/or shape memory alloy materials. The term "radiopaque" refers to a non-toxic material capable of being monitored or detected during injection into a mammalian subject by, for example, radiography or fluoroscopy. The radiopaque material may be either water soluble or water insoluble. Examples of water soluble radiopaque materials include metrizamide, iopamidol, iothalamate sodium, iodomide sodium, and meglumine. Examples of water insoluble radiopaque materials include tantalum, tantalum oxide, and barium sulfate, which are commercially available in the proper form for in vivo use. Other water insoluble radiopaque materials include, but are not limited to, gold, tungsten, stainless steel, and platinum. The coils 43 of the crossbars 34, 36, 38, 40 and the coil 56 of the delivery bar 54 may be made of the same or similar materials.

In a preferred embodiment, the coils or tubular members 30 of the frames 22, 24 are made of platinum or Nitinol. Preferably, the retention members 32, 35, 58 used for linking components of the above-described closure device 20 include or are made from a suitable shape memory alloy materials. In a preferred embodiment, the retention members 32, 35, 58 are wires that are made from a Nitinol alloy.

Radiopaque marker materials may be used in the device components directly or they may be added to one or more components of the closure device 20 so as to render them radiopaque or MRI compatible. In particular, radiopaque materials, fillers, metallic marker bands or powders may be included into one or more of the coils 30 of the frames 22, 24, the retention members 32, 35, 58, the sheets 26, 28 of biocompatible material, the coils 43 of the crossbars 34, 36, 38, 40, the coil 56 of the delivery bar 54, and/or the delivery catheter to facilitate radiographic visualization of the device during the implantation process. Preferably, one or more of the frame coils 30, crossbar coils 43, and/or delivery bar coil 56 is made from or includes a radiopaque material (such as platinum) to facilitate radiographic visualization.

Exemplary radiopaque marker materials include but are not limited to, platinum, gold, tungsten, tantalum, tantalum powder, bismuth, bismuth oxychloride, barium, barium sulphate, iodine and the like. Metallic bands of stainless steel, tantalum, platinum, gold, or other suitable materials, can include a dimple pattern, which can further facilitate ultrasound or X-ray identification.

Radiopaque markers may be introduced in any form suitable for the rendering the closure device radiopaque or MRI compatible. In addition, the radiopaque materials can be incorporated in the closure device or assembly components by a variety of common methods, such as adhesive bonding, lamination between two material layers, vapor deposition, and the materials and methods described in U.S. Pat. Appl. Publ. No. 2003/0206860, the disclosure of which is incorporated herein by reference.

Sutures 29 for linking elements of the closure device 20 to one another may be made from a variety of suture types, including braided or monofilament. Sutures 29 may be made from polyester, polypropylene, polyglycolic acid, polytetrafluoroethylene (PTFE), SIS, nylon, silk or any of a variety of absorbable or nonabsorbable suture materials known in the art. The sutures 29 may be treated or coated with radiopaque materials to facilitate visualization of the device by radiography or fluoroscopy. The sutures 29 may also be coated with antibiotics or other antimicrobial agents. Exemplary suture materials include TEVDEK II®, a braided polyester suture material impregnated with PTFE; DEKLENE II®, a polypropylene monofilament suture material, and nylon monofilament suture material, all of which are manufactured by Genzyme Biosurgery of Cambridge, Mass. Preferred suture materials include non-absorbable polypropylene sutures, such as PROLENE™ 6-0 mil (0.1524 mm) diameter (Ethicon Inc., Piscataway, N.J.).

As an alternative to sutures 29, tissue adhesives may be used to link elements of the above disclosed closure device 20 to one another, for example, to link the sheets 26, 28 of biocompatible sheet material to the frames 22, 24. An exemplary tissue adhesive is BioGlue® (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) Am. Fam. Physician 61:1383-1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); Bioglass (U.S. Biomaterials, Alachua, Fla.); CoStasis (Cohesion Technologies); MedPro Month (1999) 9:261-262; and MedPro Month (2000) 10:86-91.

Figure 9:
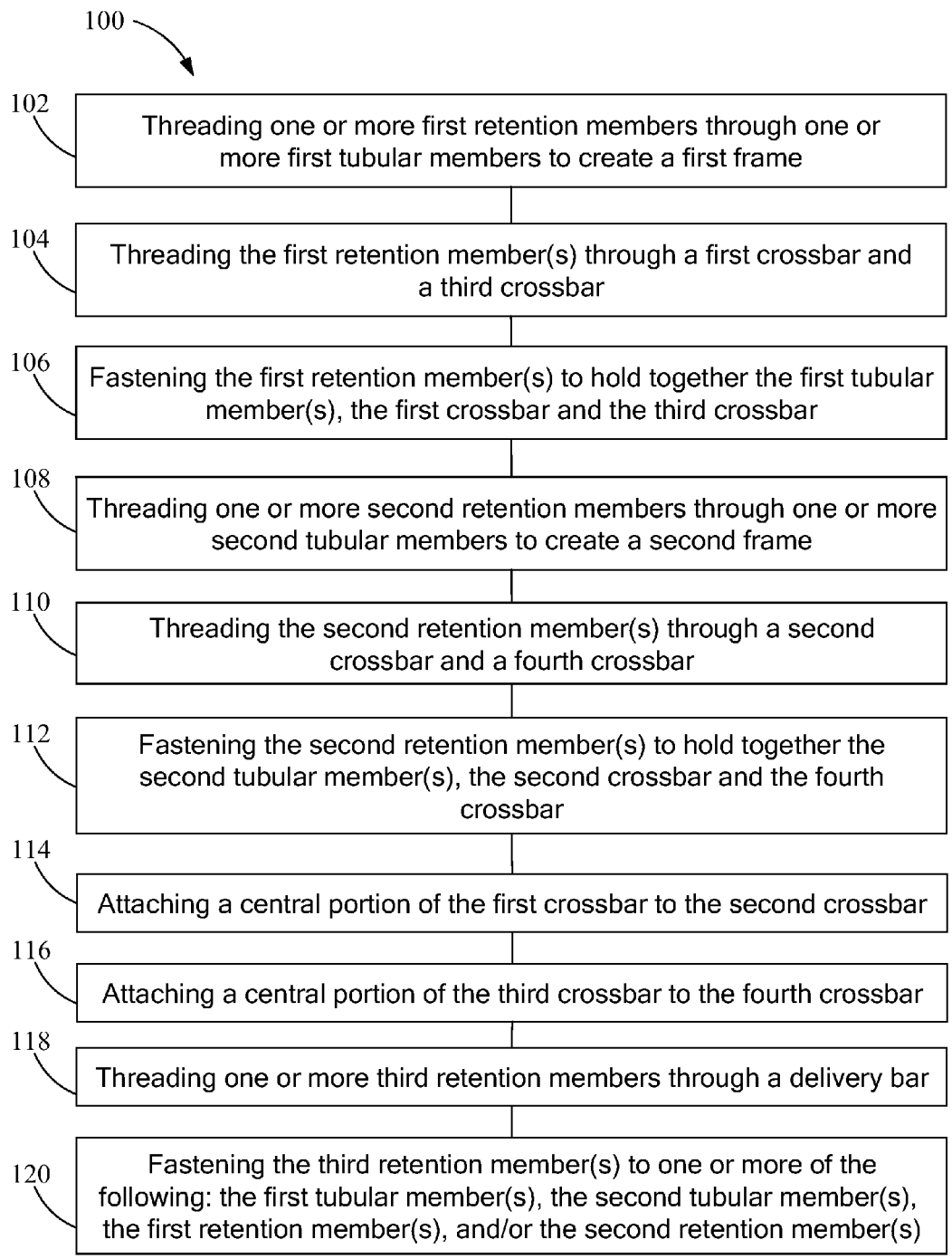
FIG. 9 is a block diagram illustrating a method for making a closure device according to the principles of the present invention.
Figure 9A:
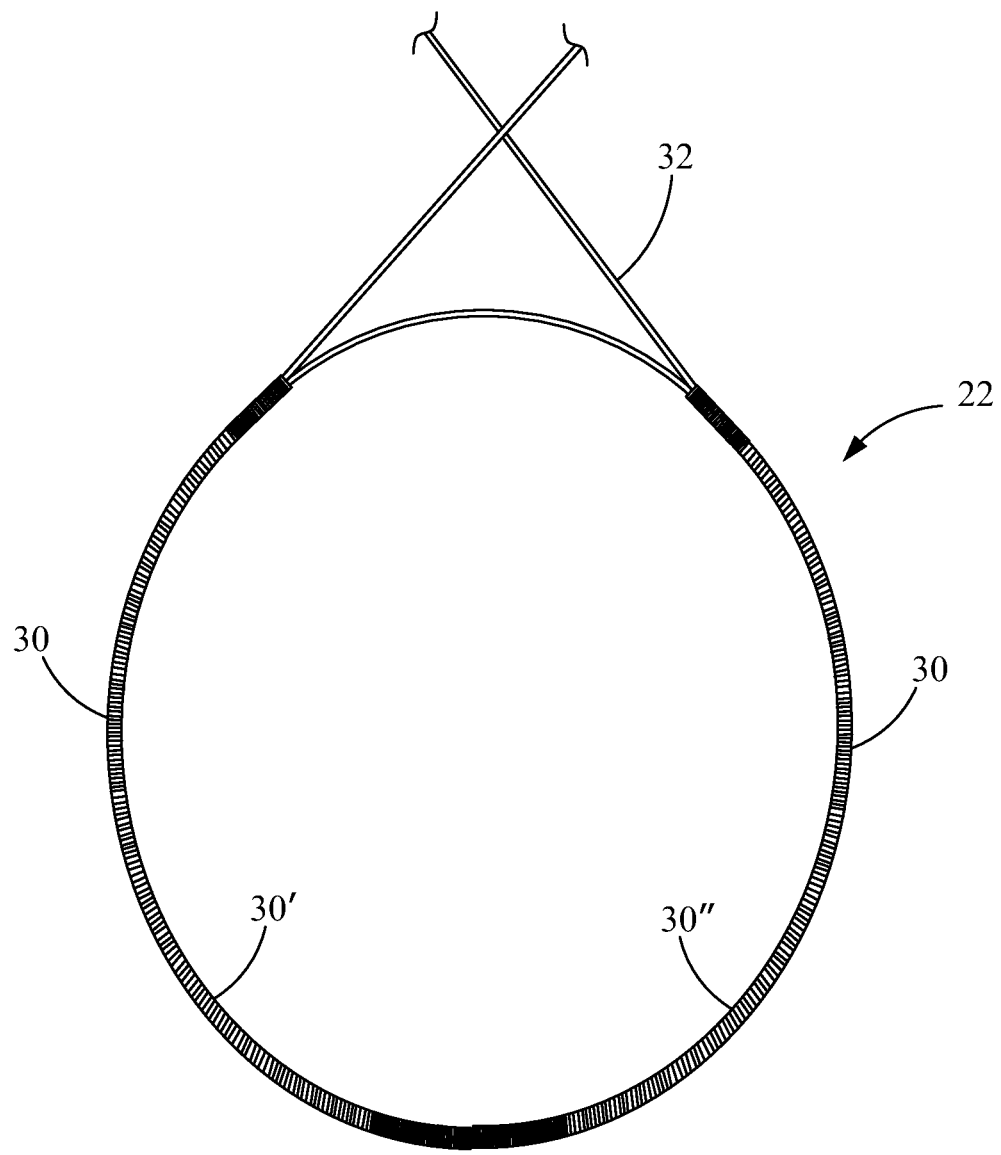
FIG. 9A is a plan view of a retention member and tubular members for constructing a frame of a closure device in accordance with the principles of the present invention.
Figure 9B:
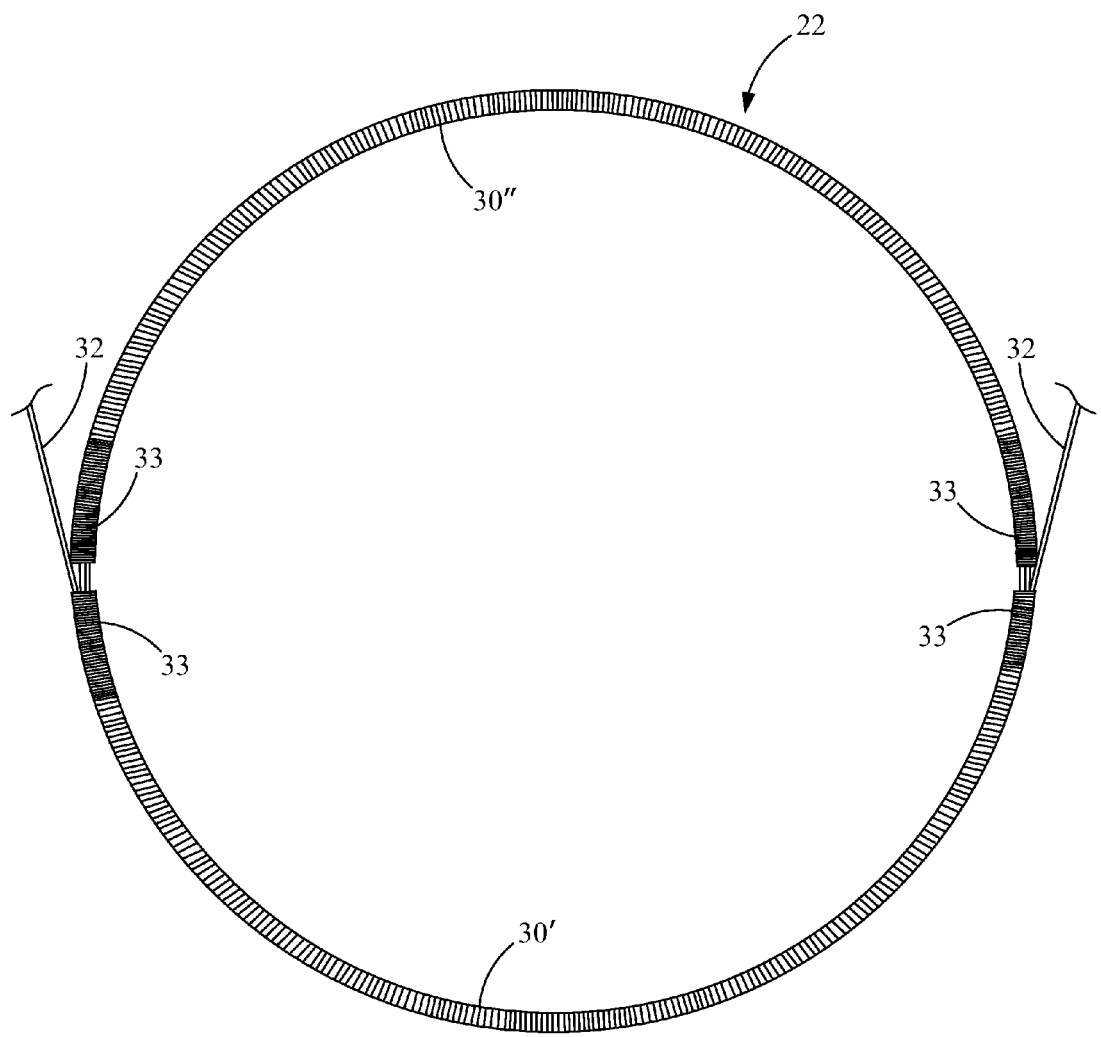
FIG. 9B is a plan view of the tubular members and retention member of FIG. 9A, forming a frame for a closure device according to the principles of the present invention.
Figure 9C:
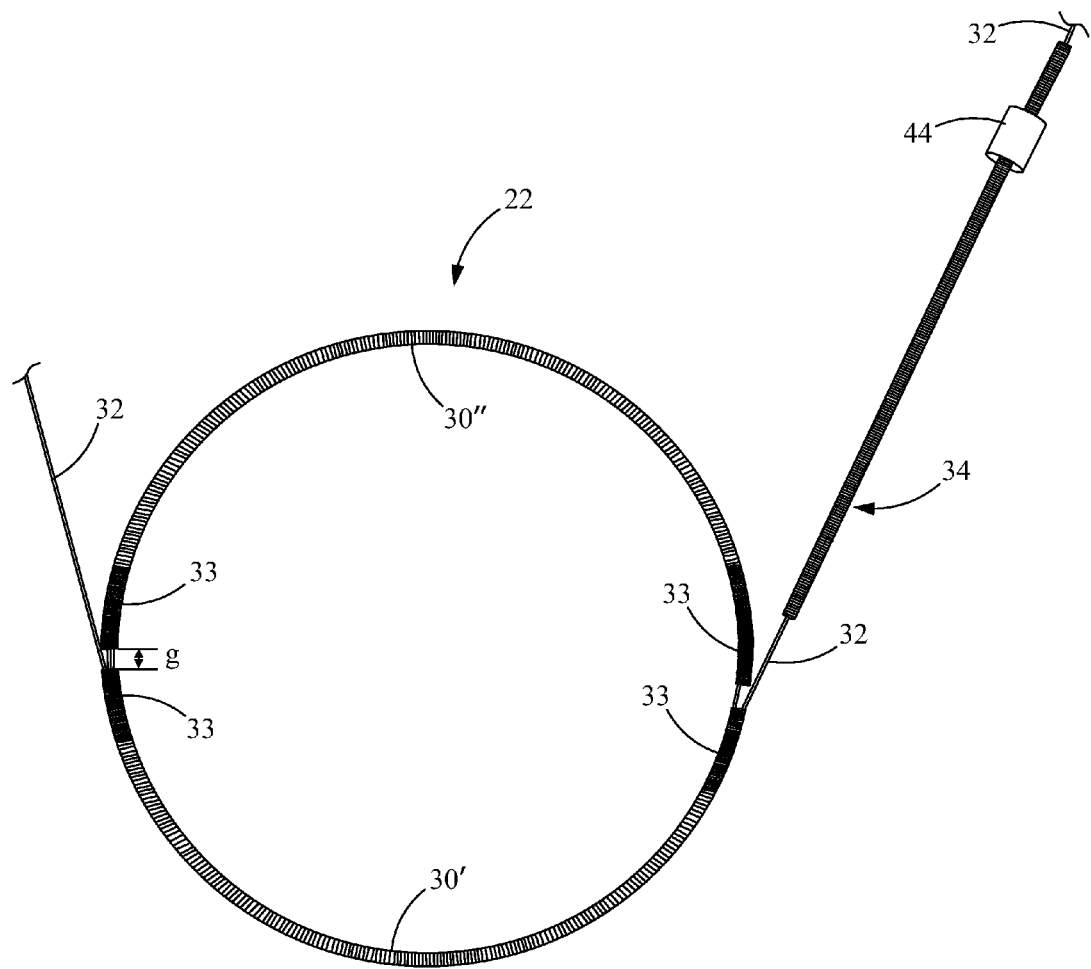
FIG. 9C is a plan view of the tubular members and retention member of FIGS. 9A-9B, and a crossbar for constructing a closure device in accordance with the principles of the present invention.
Figure 9D:
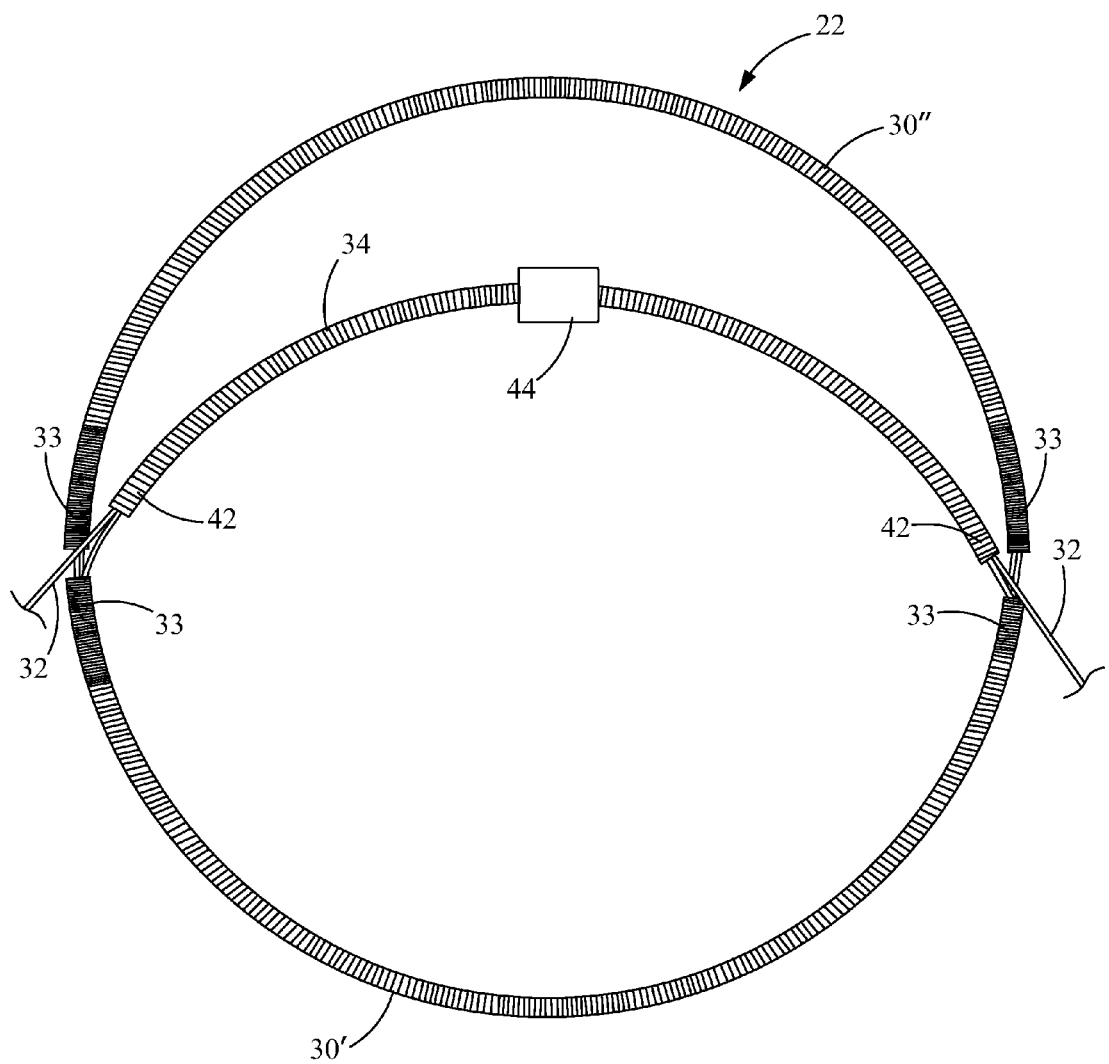
FIG. 9D is a plan view of the tubular members, retention member, and crossbar of FIG. 9C, showing the crossbar pulled into place to construct a closure device according to the principles of the present invention.
Figure 9E:
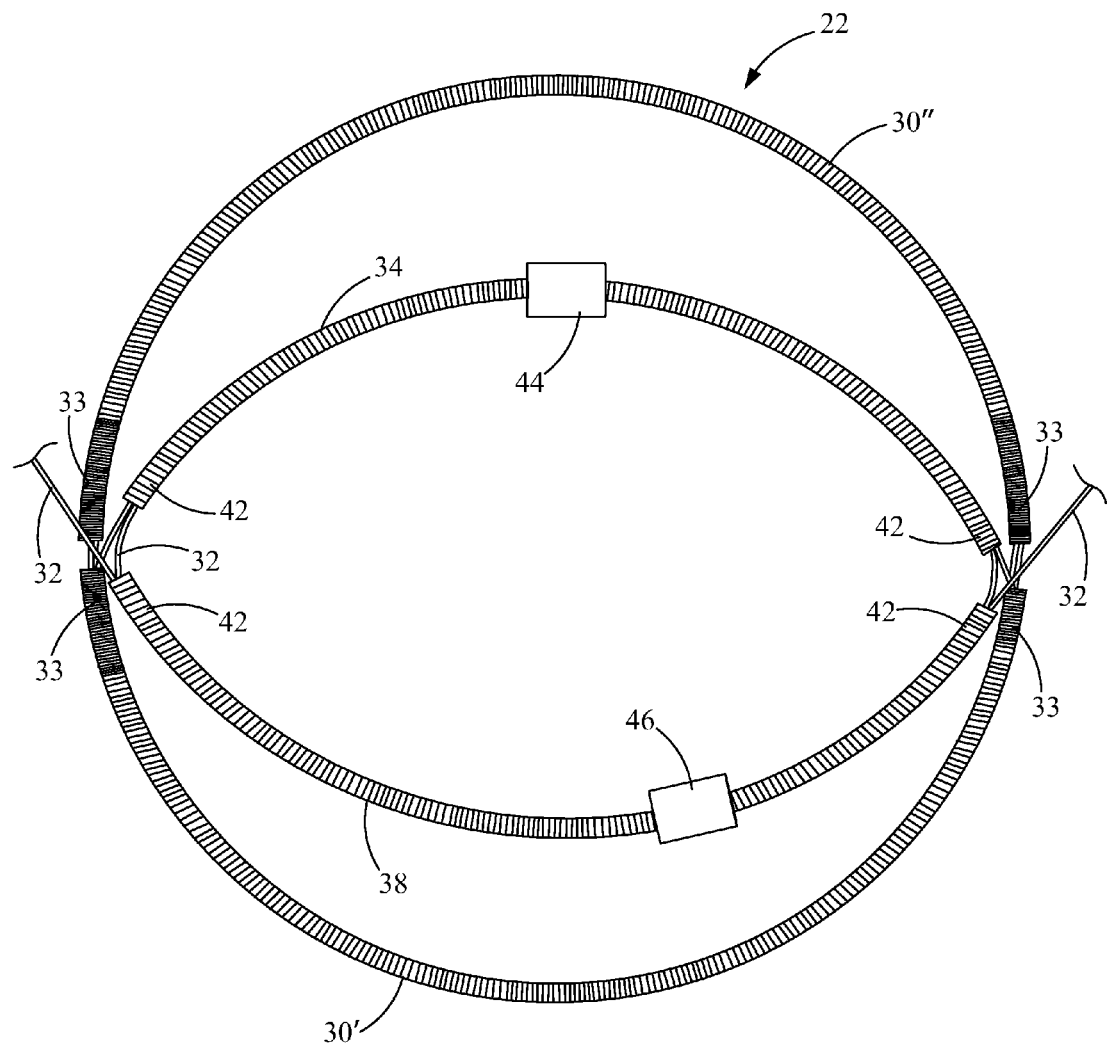
FIG. 9E is a plan view of the tubular members, retention member and crossbar of FIGS. 9C-9D, with an additional crossbar for constructing a closure device in accordance with the principles of the present invention.
Figure 9F:
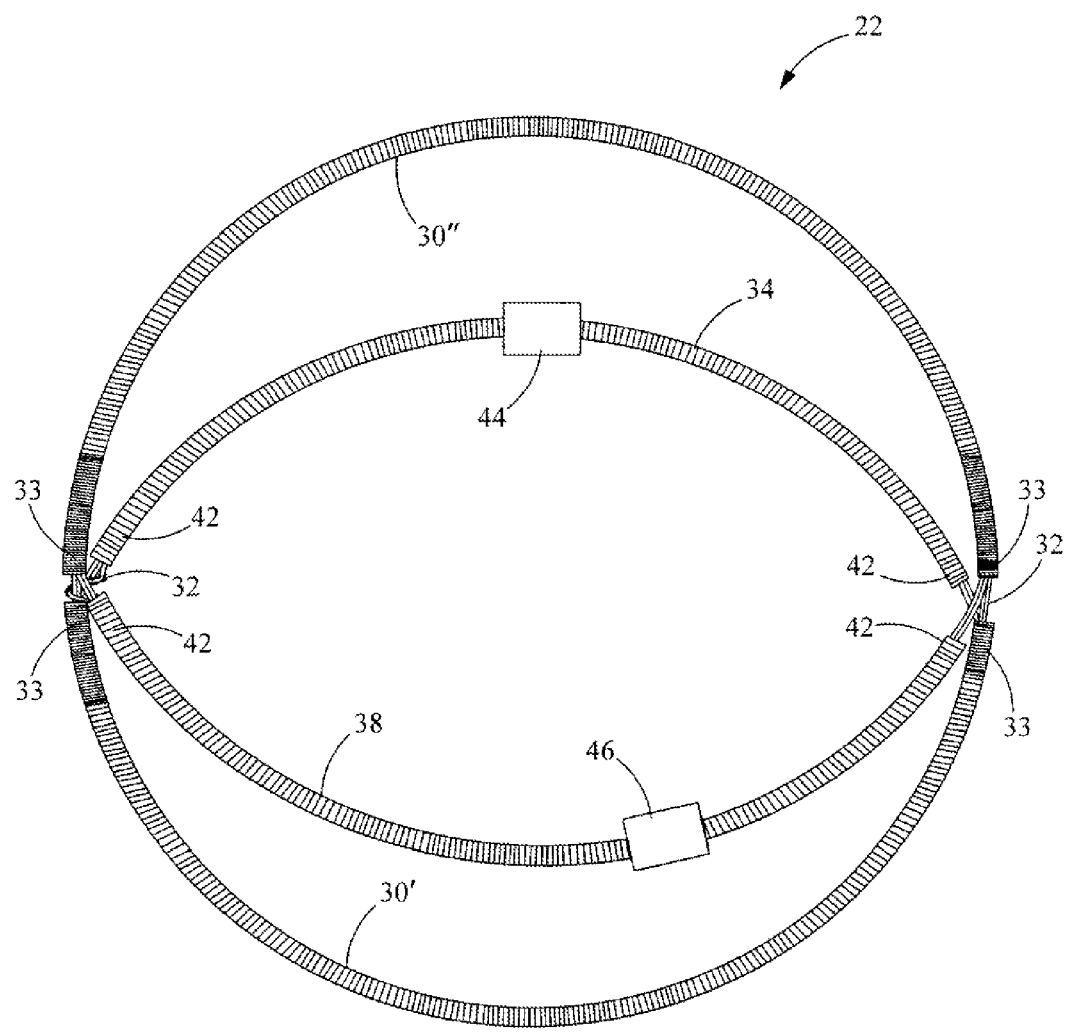
FIG. 9F is a plan view of the tubular members, retention member, and crossbars of FIG. 9E, fastened together to construct a frame and crossbar assembly for a closure device in accordance with the principles of the present invention.
Figure 9G:
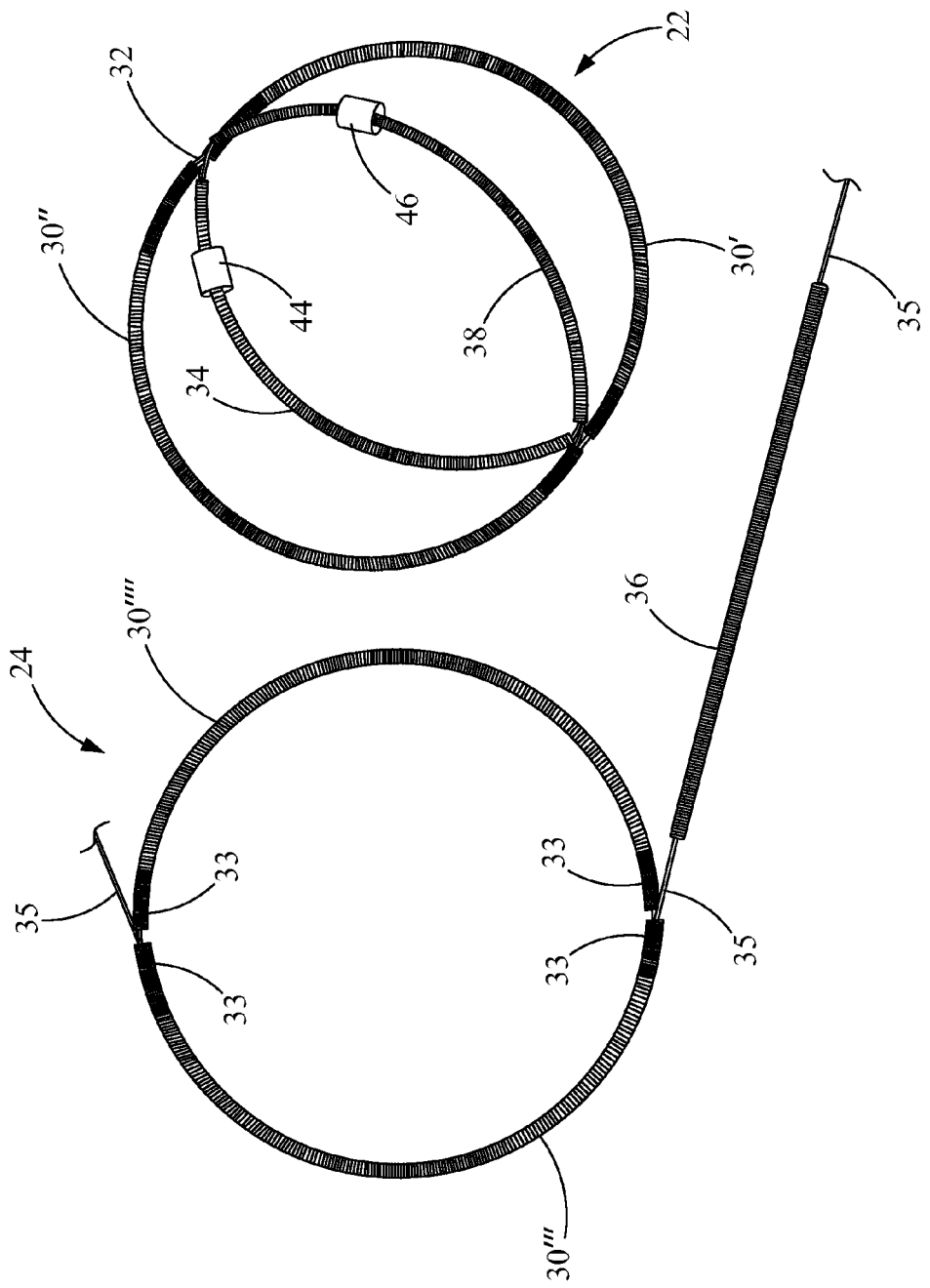
FIG. 9G is a plan view of the frame and crossbar assembly of FIG. 9F and a second set of tubular members, retention member, and additional crossbar to construct another frame and crossbar assembly to construct a closure device, according to the principles of the present invention.
Figure 9H:
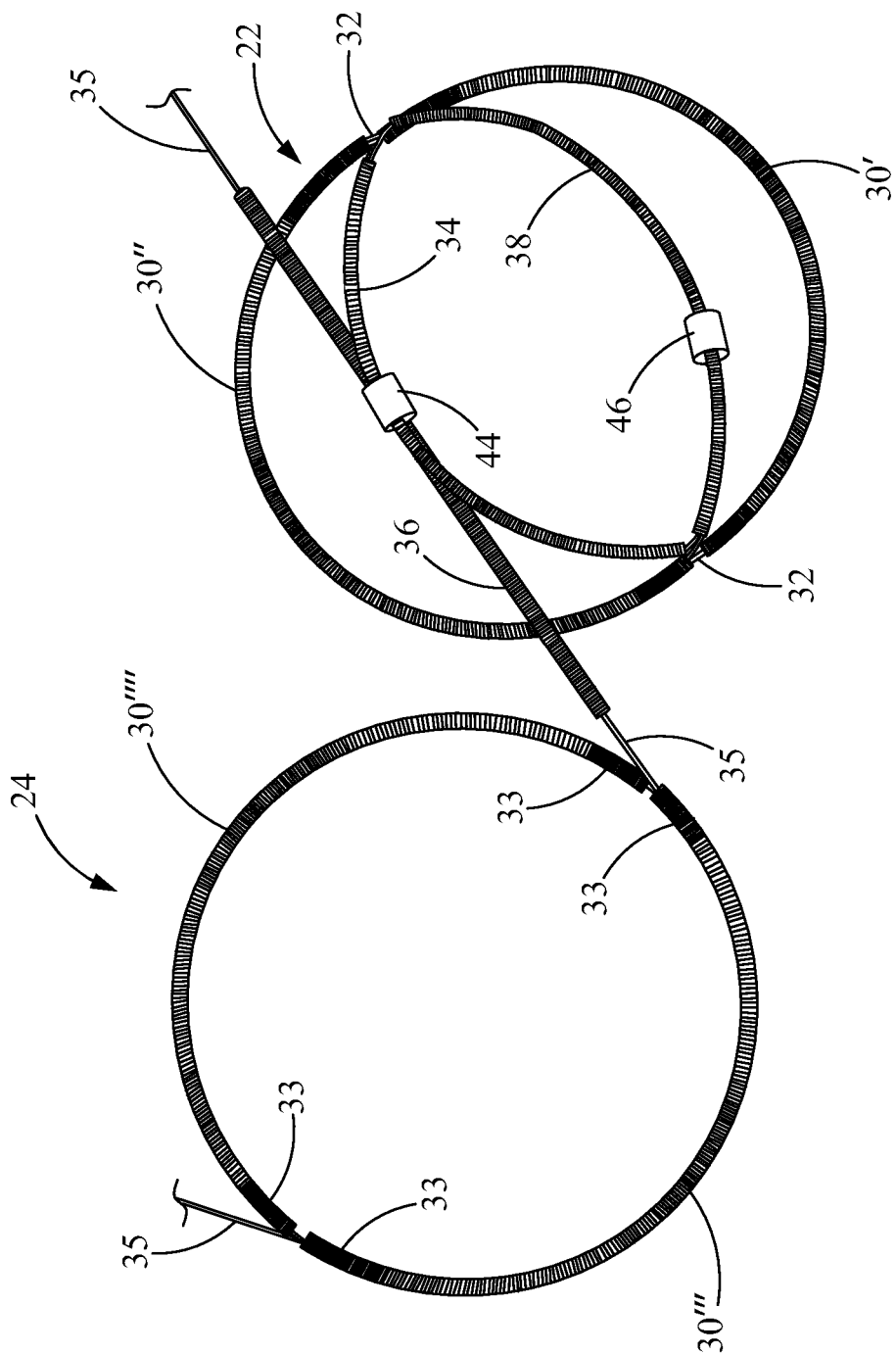
FIG. 9H is a plan view of the frame and crossbar assembly, second set of tubular members, retention member, and additional crossbar of FIG. 9G, with the additional crossbar threaded through a coupling member of the frame and crossbar assembly to construct a closure device, in accordance with the principles of the present invention.
Figure 9I:
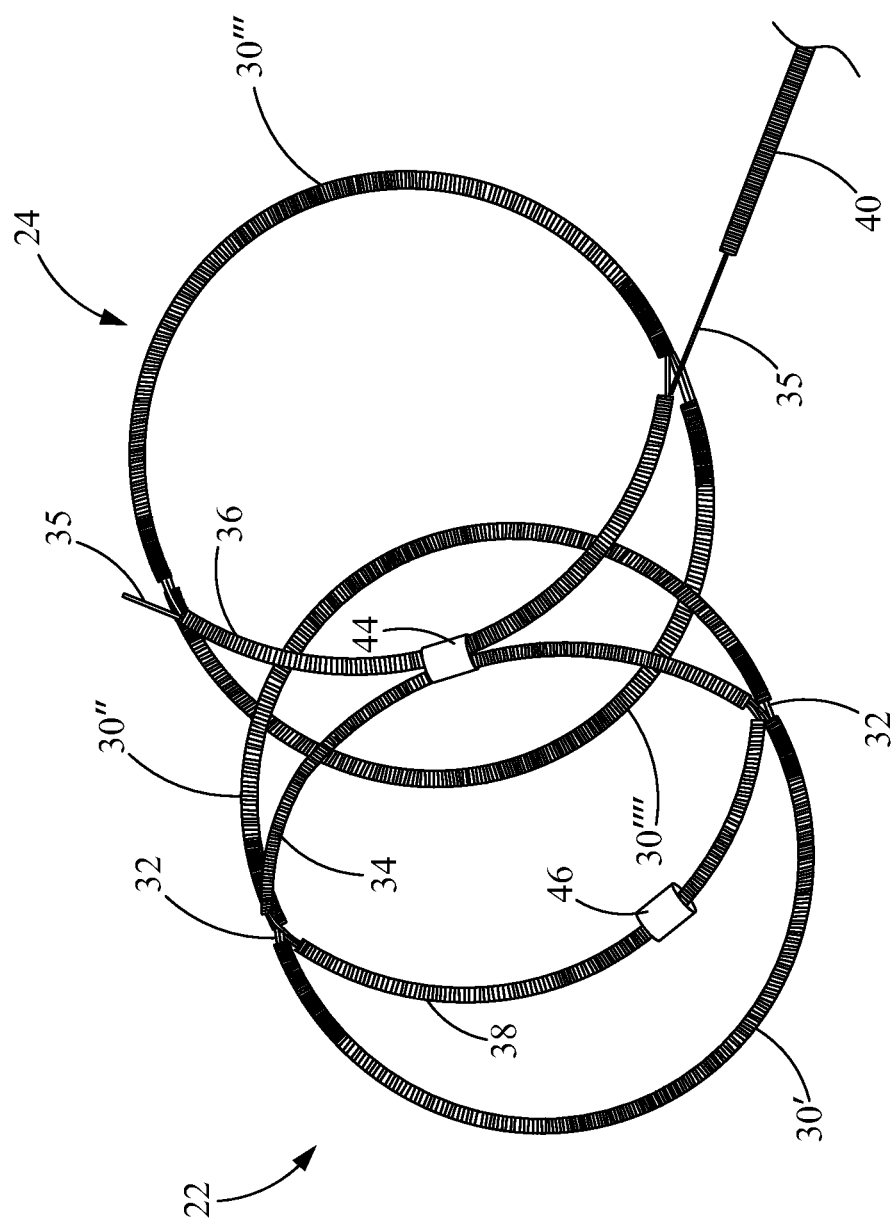
FIG. 9I is a plan view of the frame and crossbar assembly, second set of tubular members, retention member, and additional crossbar of FIGS. 9G-9H, including another additional crossbar for constructing a closure device, according to the principles of the present invention.
Figure 9J:
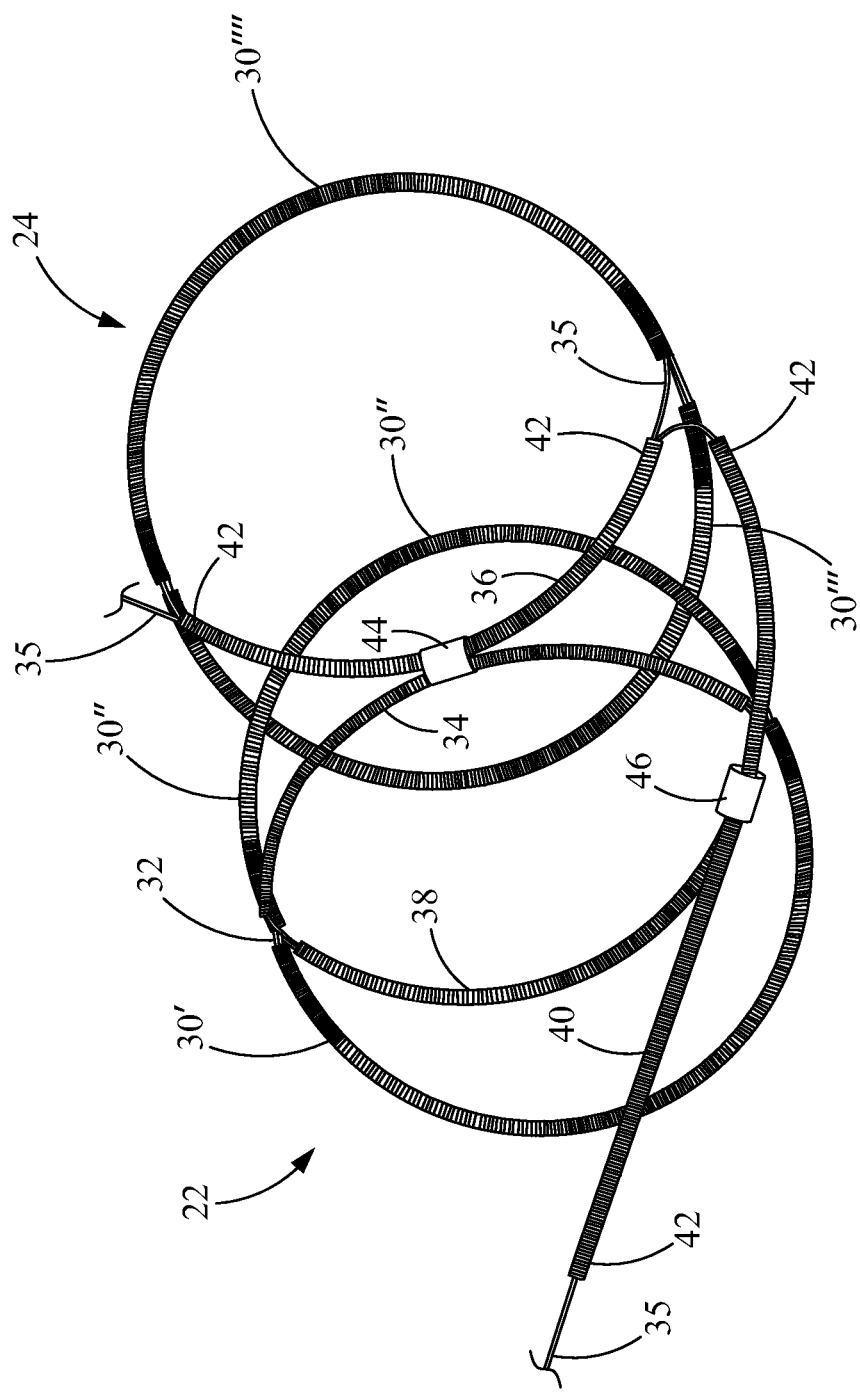
FIG. 9J is a plan view of the frame and crossbar assembly, tubular members, retention member, and crossbars of FIG. 9I, with the additional crossbar threaded through a coupling member to construct a closure device, in accordance with the principles of the present invention.
Figure 9K:
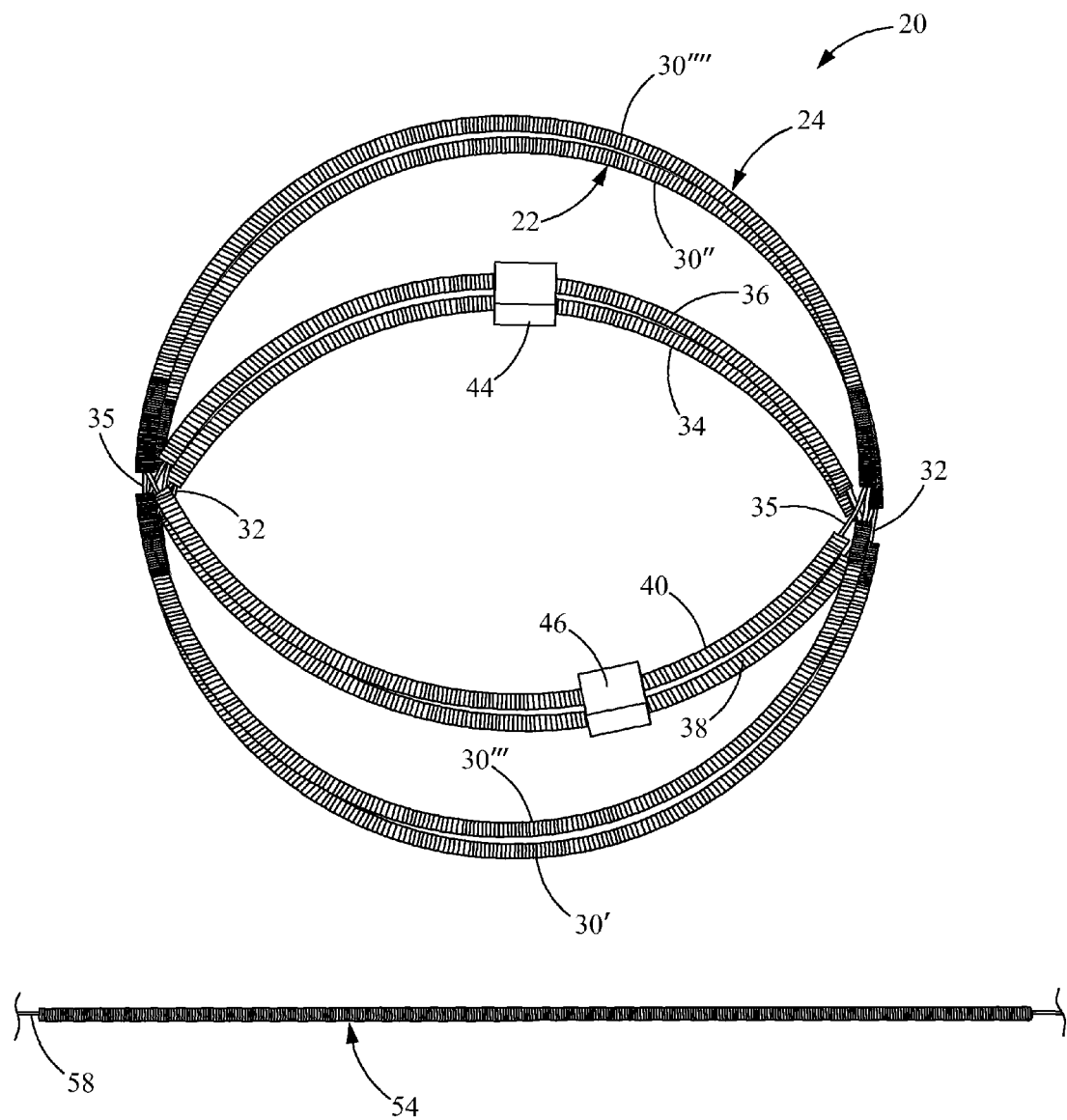
FIG. 9K is a plan view of a frame and crossbar assembly including the elements of FIGS. 9I-9J for constructing a closure device, according to the principles of the present invention.
Figure 9L:
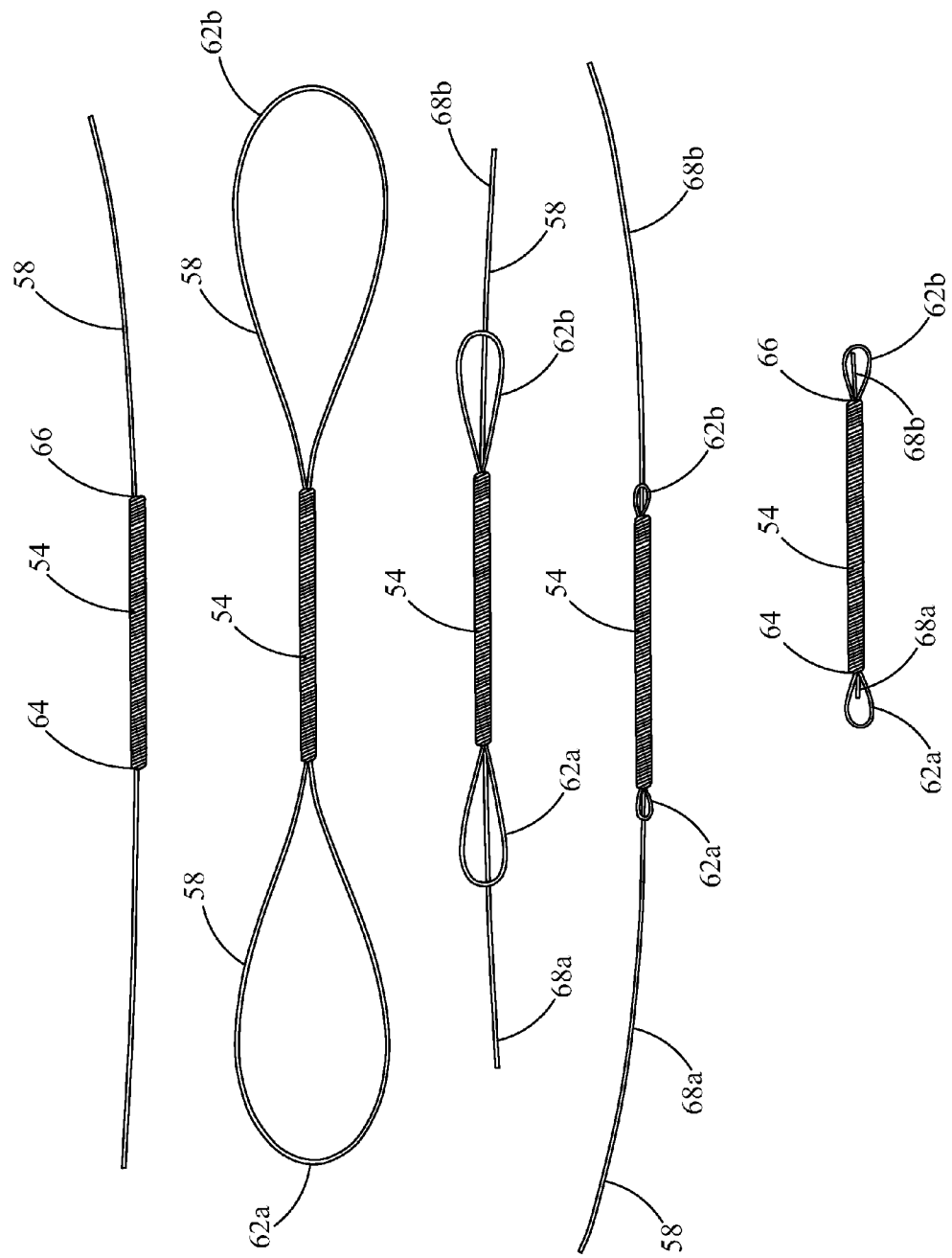
FIG. 9L illustrates a method for forming a delivery bar for constructing a closure device, in accordance with the principles of the present invention.
Figure 9M:
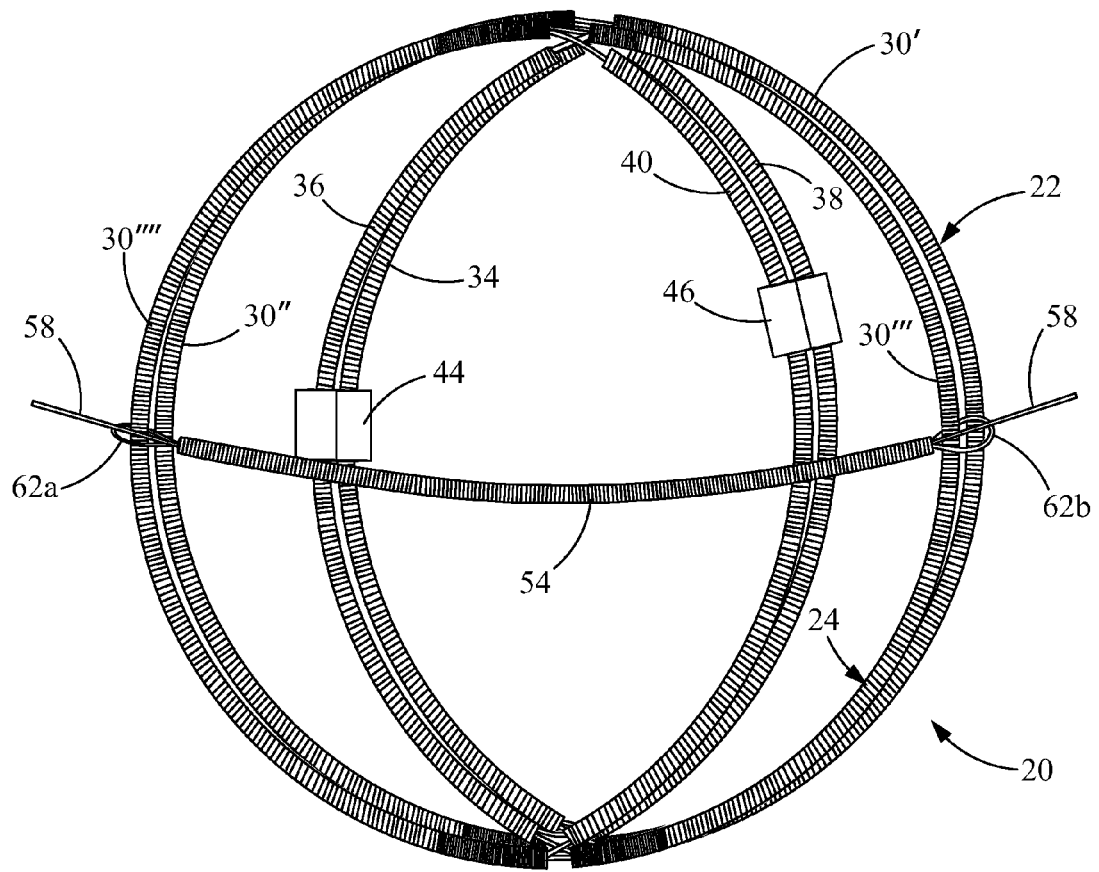
FIG. 9M is a plan view of the frame and crossbar assembly of FIG. 9K, including the delivery bar of FIG. 9L, for constructing a closure device according to the principles of the present invention.
Figure 9N:
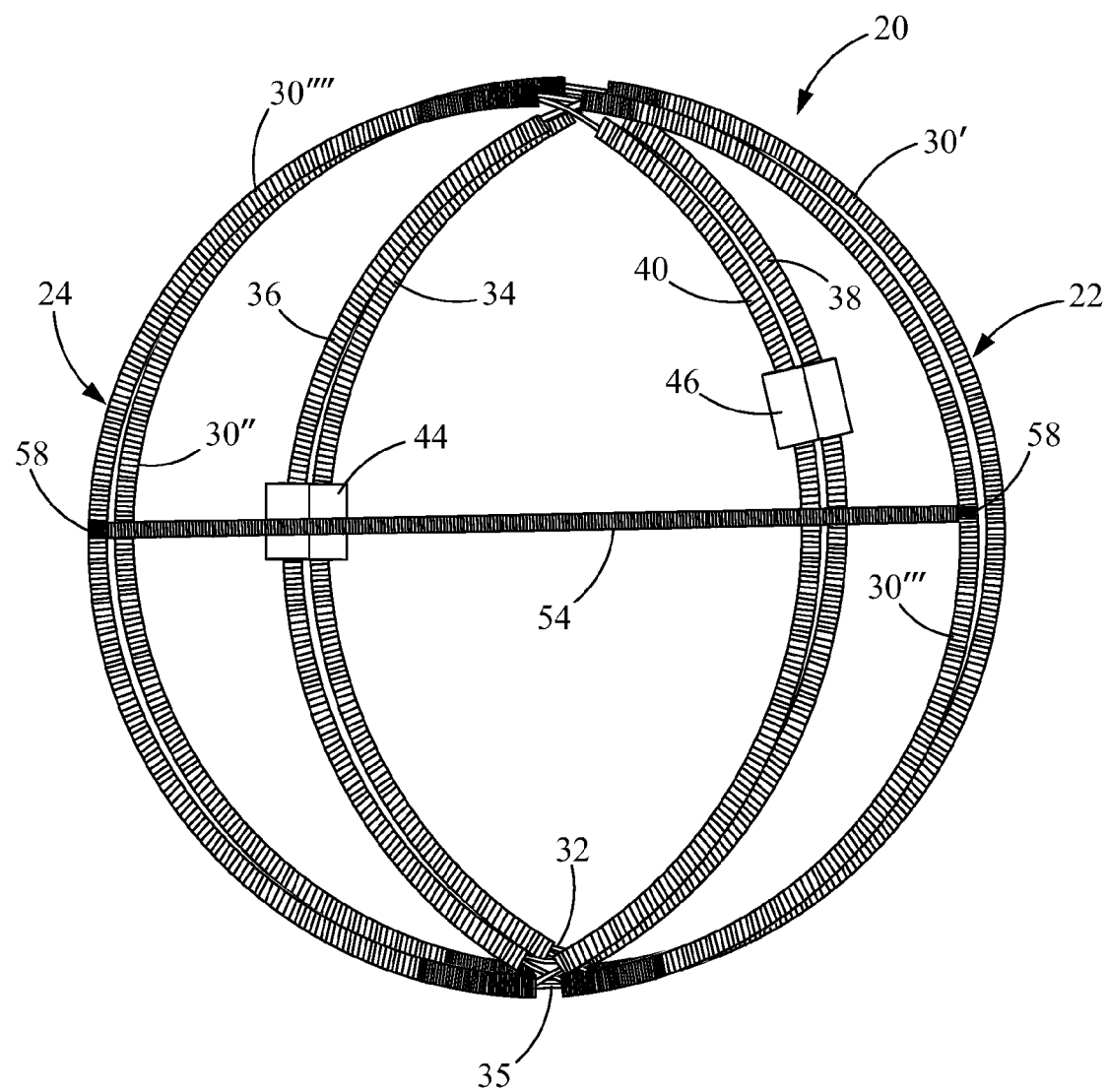
FIG. 9N is a plan view of the frame, crossbar, and deliver bar assembly of FIG. 9M, with the delivery bar secured to a frame to construct a closure device, in accordance with the principles of the present invention.

Now with reference to FIGS. 9 and 9A-9N, an embodiment of a method 100 of making a closure device 20 in accordance with the principles of the present invention is illustrated. The method 100 includes a step 102 of threading one or more first retention members 32 through one or more tubular members 30 to create a first frame 22. The tubular members 30 may be provided as coils, and the retention members 32 may be provided as wires, as described above. In this embodiment, two coils 30 (30' and 30") are threaded onto a single wire 32. As shown in FIG. 9A, the wires 32 are threaded through each coil 30 twice, such that portions of the wire 30 run through the lumen of each coil 30 twice. The wire 32 is pulled to circularize the coils 30 and form them into a ring shape, each frame coil 30 defining a hemispheric coil ring portion.

Now with reference to FIG. 9B, in this embodiment, the wire 32 is threaded through one of the coils 30 a third time, so that the ends of the wire 32 extend from the first frame 22 at opposite sides of the frame 22. The wire 32 is pulled to bring the ends 33 of each of the coils 30', 30" close together with substantially no gap g, or a very small gap g between the ends 33. At this time, the diameter of the frame 22 may be verified to determine whether the diameter is the appropriate size for the desired application of the closure device 20.

With reference to FIGS. 9 and 9C-9E, the method 100 includes a step 104 of threading the first retention member(s) 32 through a first crossbar 34 and a third crossbar 38. The first crossbar 34 may be provided as a coil, as explained above. Although a single first retention member 32 is described herein for connecting the frame coils 30 and the first crossbar 34, it should be understood that a plurality of retention members 32 could be used. In some embodiments, the method 100 could include a step of disposing a coupling member 44, such as a marker band, onto the first crossbar 34.

With reference to FIG. 9D, another end of the retention member, wire 32, formerly shown on the left side of the page in FIG. 9C is also threaded through the first crossbar 34. As such, the wire 32 is runs through the lumen of the first crossbar 34 twice, and extends from each terminal end 42 of the first crossbar 34 at opposite sides of the first frame 22. The terminal ends 42 are pulled close to the ends 33 of the frame coils 30', 30".

Now with reference to FIG. 9E, a "third" crossbar 38 (the second crossbar 36 has not yet been added to the closure device 20, and it will be described below) is threaded onto the wire 32. The wire 32 is threaded through the lumen of the third crossbar 38 twice, from each side of the frame 22. Therefore, the wire 32 end shown at the right side of FIG. 9D now appears on the left side of FIG. 9E after being threaded through the lumen of the coil of the third crossbar 38, and the wire 32 end shown at the left side of FIG. 9D now appears on the right side of FIG. 9E after being threaded through the lumen of the coil of the third crossbar 38. The wire 32 is pulled tight to bring the terminal ends 42 of the third crossbar 38 near the terminal ends 42 of the first crossbar 34 and the ends 33 of the first frame coils 30', 30" Prior to threading the third crossbar 38 onto the wire 32, a coupling member 46, such as a marker band, may be threaded onto the third crossbar 38.

Thereafter, the wire 32 may be fastened, or it may be threaded through one or more of the frame coils 30', 30", or coils of the first and third crossbars 34, 38 as space within the lumens permits. For example, the wire 32 as shown in FIG. 9E may be threaded back through the coil 30", from the right side of FIG. 9E to the left side, so that each wire 32 end is located on the left side of the figure. After such threading, the wire 32 will then be threaded through each of the frame coils 30', 30"a total of three times, which may be the maximum of amount of wire for which there is space in the lumens in some embodiments. For example, in some embodiments, the frame coils 30', 30" and crossbars 34, 38 may comprise 0.023 inch diameter Platinum coil, and the wire 32 may comprise 0.0065 inch diameter Nitinol wire, by way of example.

At this time, since the crossbars 34, 38 still only have the wire 32 threaded through each of them twice thus far, one end of the wire 32 could then be threaded through the first crossbar 34, while the other end of the wire 32 could be threaded through the third crossbar 38. Accordingly, both ends of the wire would then be located on the right side of FIG. 9E.

In some embodiments, one or both ends of the wire 32 may be wrapped around the left edge of the frame 22 before it is threaded back through the crossbars 34, 38 for a third run through the crossbars 34, 38. For example, referring to FIG. 9F, the wire 32 can be seen wrapped around a side of the frame 22. In this embodiment, the wire 32 is wrapped around strands of itself, however, the wire could be wrapped around one or both of the coils 30', 30". The wire 32 ends may be cut or clipped, with wire cutters for example, as close as possible to the frame coils 30', 30".

The method 100 includes a step 106 of fastening the first retention member(s) 32 to hold together the first tubular member(s) (coils 30', 30"), the first crossbar 34, and the third crossbar 38. Accordingly, the ends of the wire 32, the frame coils 30', 30", and/or the coils of the crossbars 34, 38 may be crimped with pliers to hold the wires 32 in place; however, it should be understood that the wires 32 could be fastened in any other suitable manner, such as by welding, soldering, tying, press-fitting them back into one of the coils 30', 30" or crossbars 34, 38, or using adhesives, by way of example. The coils 30', 30" may be pulled to remove most of any gap or exposed wire 32, as shown in FIG. 9F.

The method 100 further includes a step 108 of threading one or more second retention members 35 through one or more second tubular members 30''', 30'''' to create a second frame 24. With reference to FIG. 9G, in this embodiment, a single wire is used as the second retention member 35. The wire 35 is threaded through two coils 30''', 30'''', each comprising a portion of the second frame 24. The wire 35 is threaded through one of the second frame members 30'''' twice and the other second frame member 30'''' three times, similarly to the threading of the first frame 22 described in FIG. 9C. The wire 35 is pulled tight to bring the ends 33 of the coils 30''', 30'''' together and form the frame coils 30''', 30'''' into a ring shape, each frame coil 30''', 30'''' defining a hemispheric coil ring portion.

In addition, the method 100 includes a step 110 of threading the second retention member(s) 35 through a second crossbar 36 and a fourth crossbar 40. In FIG. 9G, the wire 35 is shown threaded through the lumen of the second crossbar 36, which may be a coil, as described above. The second crossbar 36 is not provided with its own coupling member because it will share a coupling member located on the first crossbar 34. The addition of the fourth crossbar 40 will be described below.

With reference to FIGS. 9 and 9H, the method 100 includes a step 114 of attaching a central portion of the first crossbar 34 to the second crossbar 36. In this embodiment, the second crossbar 36 is threaded through the coupling member 44 that is located around the first crossbar 34. It should be understood that the first and second crossbars 34, 36 could additionally or alternatively be attached to each other by other suitable means, some of which are described above.

Thereafter, the end of the wire 35 located at the left side of FIG. 9H may be threaded through the second crossbar 36 such that the wire 35 passes through the lumen of the second crossbar 35 twice, similarly to the way the first crossbar 38 was threaded as shown in FIG. 9D. For example, referring now to FIG. 9I, the wire 35 is shown threaded through the second crossbar 36 twice. In addition, FIG. 9I shows the wire 35 being threaded through the fourth crossbar 40. In FIG. 9I, the closure device 20 has been flipped 180° from the orientation in which it was shown in FIG. H. Like the second crossbar 36, the fourth crossbar 40 does not have its own coupling member because it will share a coupling member with the third crossbar 38.

Referring now to FIGS. 9 and 9J, the method 100 includes a step 116 of attaching the third crossbar 38 to the fourth crossbar 40. In this embodiment, the fourth crossbar 40 is threaded through the coupling member 46 located around the third crossbar 38 to attach the third crossbar 38 to the fourth crossbar 40. The wire 35 end that is not already threaded through the fourth crossbar 40 may then be threaded through the lumen of the fourth crossbar 40. Both free ends of the wire 35 may then be pulled to substantially cover the exposed portions of the wire 35 with coils. The terminal ends 42 of the second and fourth crossbars 36, 40 may be pulled near the ends 33 of the coils 30''', 30'''', similarly to the configuration of the first frame 22, the first crossbar 34, and the third crossbar 38, as shown in FIG. 9E.

The wire 35 may be optionally threaded through one or more of the coils 30''', 30'''' and/or the second and fourth crossbars 36, 40 again, as desired. For example, one end of the wire 35 may be threaded through the coil 30'''', such that the wire 35 is then threaded through each of the second frame coils 30''', 30'''' three times. The ends of the wire 35 will then be located on the same side of the second frame 24. One end of the wire 35 may then be threaded once more through each of the second and fourth crossbars 36, 40, resulting in the wire 35 being threaded through each of the second and fourth crossbars 36, 40 a total of three times. Prior to being threaded through the crossbars 36, 40 a third time, one or both ends of the wire 35 could be wrapped around the coils 30''', 30'''' or wire 35 of the second frame 24, if desired.

Referring now to FIGS. 9 and 9K, the method 100 further includes a step 112 of fastening the second retention member(s) 35 to hold together the second tubular member(s) 30''', 30'''', the second crossbar 36, and the fourth crossbar 40. The wires 35 are pulled tight, cut, and fastened, for example, by crimping or other suitable means, such as those described above with respect to fastening the wire 32 of the first frame 22. In some embodiments, one or more of the coils 30''', 30'''' of the frames 22, 24 or the coils of the crossbars 36, 40 may be crimped to hold the wire 35 in place. The frame coils 30''', 30'''' may be stretched to substantially cover the exposed portions of the wire 35.

The coupling members 44, 46 may be slid onto a central portion of the crossbars 34, 36, 38, 40, for example, a portion not more than 30% from the geometric center of the crossbars 34, 36, 38, 40, by way of example. The coupling members 44, 46 may be partially flattened to tighten them around the crossbars 34, 36, 38, 40, for example, by crimping, but preferably the coupling members are not crimped so tight as to kink the coils of the crossbars 34, 36, 38, 40. In addition, or in the alternative, sutures may be secured around the coupling members 44, 46 to hold them in place. It should be understood that the first and second crossbars 34, 36 and the third and fourth crossbars 38, 40 may be attached to each other in any other suitable manner, and they need not use coupling members 44, 46; and the coupling members 44, 46 need not be marker bands.

The method 100 further includes a step 118 of threading one or more third retention members, such as a wire 58, through a delivery bar 54. In this embodiment, the delivery bar 54 includes a hollow coil through which the wire 58 is threaded.

Referring now to FIG. 9L, a method of threading the wire 58 through the coil of the delivery bar 54 is illustrated. Briefly, the delivery bar wire 58 is passed through the coil of the delivery bar 54 three times. The loop structures 62a, 62b can be formed by extending the wire 58 through the coil of the delivery bar 54, looping the wire 58 back towards each open end 64, 66 of the coil of the delivery bar 54, pulling the wire 58 at each delivery bar 54 coil end 64, 66 back through the coil of the delivery bar 54 in the opposite direction to achieve a desired loop size, and cutting off the excess free anchor wire ends 68a, 68b extending from each end 64, 66 of the coil of the delivery bar 54. The free wire ends 68a, 68b may be looped back, knotted or crimped near the ends 64, 66 of the coil of the delivery bar 54 to stabilize the terminally disposed loop structures 62a, 62b or free wire ends 68a, 68b proximal to each end 64, 66 of the coil of the delivery bar 54. By configuring the loop structures 62a, 62b to be wider than the diameter of the coil of the delivery bar 54 at each coil end 64, 66, the grasping members or loop structures 62a, 62b are frictionally engaged by or secured by the coil of the delivery bar 54.

Now referring to FIG. 9M, the loop structures 62a, 62b, shown in FIG. 9L, are looped around the frame coils 30''', 30'''' of the second frame 24. In other words, FIG. 9L shows an exemplary method of created the loop structures 62a, 62b, but in this embodiment, the loop structures 62a, 62b are created around the frame coils 30''', 30'''', rather than merely around nothing as shown in FIG. 9L.

Referring to FIGS. 9 and 9N, the method 100 further includes a step 120 of fastening the third retention member(s) 58 to one or more of the following: the first tubular member(s) 30', 30'', the second tubular member(s) 30''', 30'''', the first retention member(s) 32, and/or the second retention member(s) 35. In the embodiment of FIG. 9N, the third retention member, wire 58, is fastened around the coils 30''', 30'''' of the second frame 24, at a location spaced apart from the terminal ends 42 of the second and fourth crossbars 36, 40. The loops 62a, 62b of the wire 58 are secured around a central portion, not more than 30% from the geometric center, of the frame coils 30''', 30'''', however, it should be understood that in other embodiments, the delivery bar 54 need not be secured around central portions of the frame coils 30''', 30''''. The ends of the wires 58 are pulled tight to remove the slack and the loops 62a, 62b are wrapped snugly around the frame coils 30''', 30''''. It should be understood that the delivery bar 54 may alternatively be fastened to the second frame 24 or the first frame 22 in any other suitable manner, such as described above.

The ends of the wire 58 are cut at a location very close to the coil of the delivery bar 54. The coil of the delivery bar 54 and/or the wire 58 may be crimped to fasten the delivery bar 54 in place. The coil of the delivery bar 54 may also be stretched to substantially eliminate exposed portions of the wire 58.

The crossbars 34, 36, 38, 40, and/or the first and second frames 22, 24 may be heat treated. Heat treating the crossbars 34, 36, 38, 40 may assist with configuring the crossbars 34, 36, 38, 40 to bend toward a flat position, such as shown in FIGS. 4 and 5. Heat treating the frames 22, 24 may assist with biasing the frames toward an expanded state.

Figure 10A:
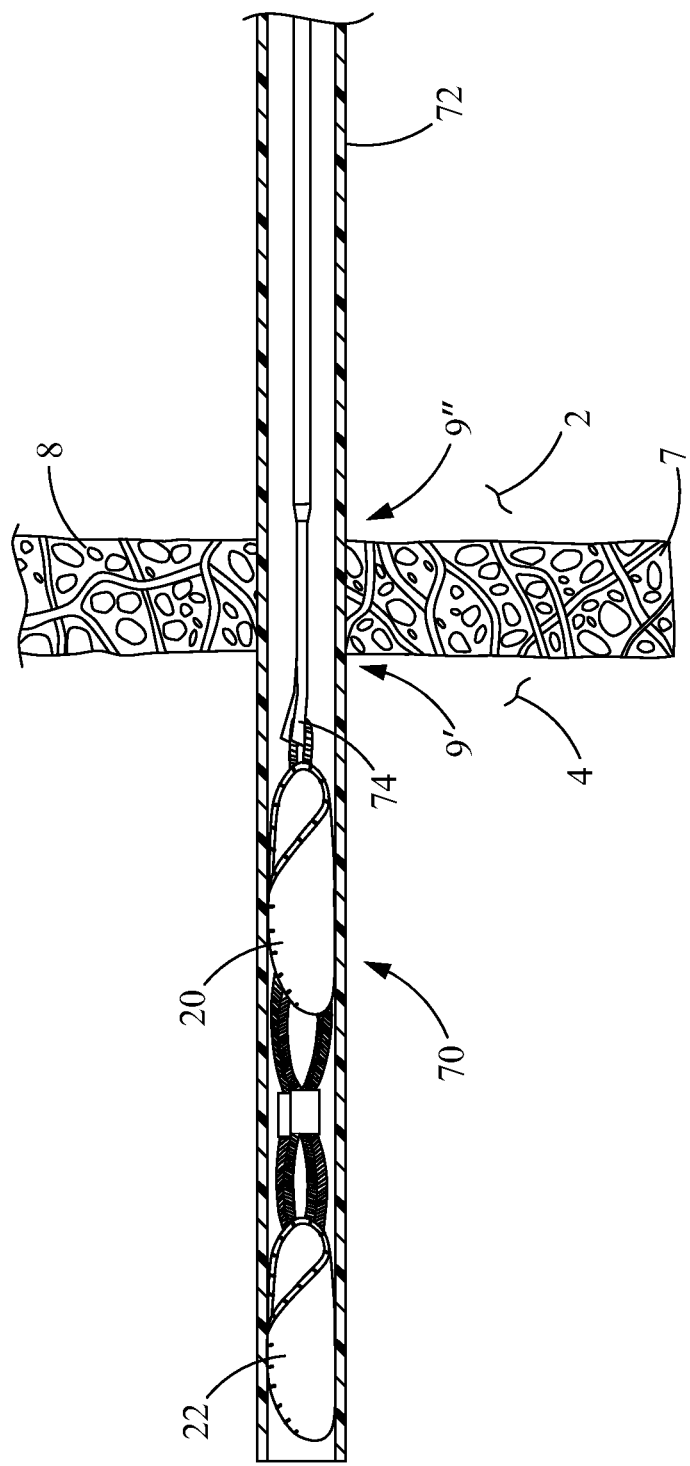
FIG. 10A is a cross-sectional view of the distal end of a closure device assembly inserted through a bodily passageway, according to the principles of the present invention.
Figure 10B:
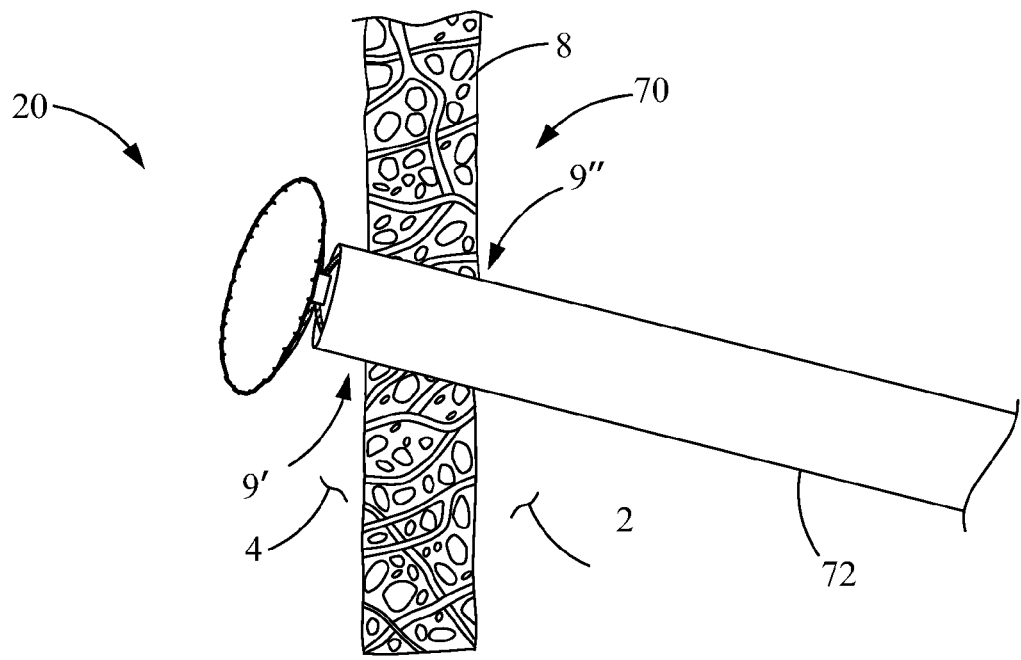
FIG. 10B is a side view of the distal end of the closure device assembly and bodily passageway of FIG. 10A, showing a closure device partially released from the distal end of the closure device assembly, in accordance with the principles of the present invention.
Figure 10C:
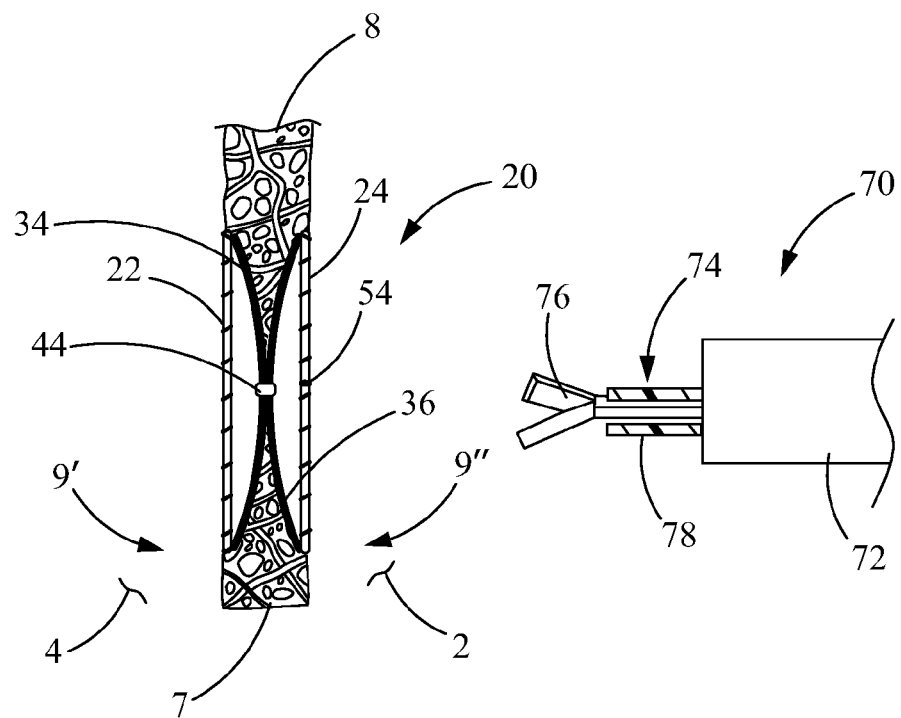
FIG. 10C is a side view of the distal end of the closure device assembly and bodily passageway of FIGS. 10A-10C, showing retraction of a locking catheter sheath and disengagement of the closure device from the delivery release member, in accordance with the principles of the present invention.

In a further aspect, referring now to FIGS. 10A-10C, a closure device assembly 70 for delivering a closure device 20 according to the present invention is provided. The closure device assembly 70 includes a delivery catheter housing 72, a delivery release member 74, and a pre-loaded, collapsibly disposed closure device 20. The delivery release member 74 includes one or more structural portions for releasable attachment to at least one portion of the closure device 20, such as a delivery bar 54. In a further aspect, the delivery release member 74 is preferably positioned in a locking catheter preventing inadvertent release of the closure device 20 when held in a compressed state inside the delivery catheter housing 72.

The delivery release member 74 may include a structure configured for releasable attachment to the delivery 54 or other portion of the closure device 20. The delivery release member 74 may be configured as an engaging member or a release member having an engaging structure complementary to the portion of the closure device 20 to which it is designed to engage, for releasable attachment thereto. For example, the delivery release member 74 may include a crossbar engaging portion, a frame engaging portion, or a delivery bar engaging portion 76. The engaging portion may include a ball, hook, loop, pair of cups or jaws, or any other suitable member capable of releasable attachment to the delivery bar 54 or other portion of the closure device 20. In one embodiment, the delivery release member 74 includes biopsy forceps. In another embodiment, the delivery release member 74 includes one or more hook-release structures.

Upon disengagement of the delivery bar 54 from the delivery release member 74, for example, the covered first frame 22 can be released so as to cover an opening of the bodily passageway, whereby the second frame 24 is secured to the opposite end of the bodily passageway, thereby sandwiching the closure device 20 around and through a bodily passageway, such as a PFO having an opening 9 between a septum primum 7 and a septum secundum 8.

In one embodiment, the delivery release member 74 includes an engaging structure 76 in the form of biopsy jaws or cups to facilitate releasable linkage to the delivery bar 54 of the closure device 20. As described above, the delivery bar 54 may be formed from a delivery bar coil 56 having a wire 58 extending longitudinally therethrough. The engaging structure 76 may be configured to releasably link to the coil 56 of the delivery bar 54, by way of example.

As described above, the closure device 20 is made from sufficiently flexible materials to enable the device 20 to be collapsibly disposed in a relatively small delivery catheter housing 72 (including 8 to 12 French). The closure device 20 may be preloaded at the tip of the delivery catheter housing 72 in an unexpanded, first configuration. When the closure device 20 is expelled from the delivery catheter housing 72, it may expand to a second, expanded configuration, particularly when the closure device 20 is made from shape memory materials. Non-shape memory materials, such as stainless steel and the like, may be used for closure devices 20 requiring a lower degree of compression or expansion upon release.

In a preferred embodiment, the closure device assembly 70 includes a delivery catheter housing 72 with a curved flexor catheter sheath, and a collapsibly disposed closure device 20 preloaded at the sheath tip and connected to a delivery release member 74, such biopsy forceps 76 or a hook held within a locking catheter 78. In a particularly preferred embodiment, the closure device assembly 70 includes a curved 8-12 French delivery catheter; a 4 or 5 French locking catheter 78 holding the biopsy forceps 76, and a collapsibly disposed closure device 20. Flexor® Introducer Sets (Cook Medical Inc., Bloomington, Ind.) provide a preferred source of delivery catheters for use in the present invention.

The delivery catheter housing 72 may be configured for "long wire" or "over-the-wire" (OTW) delivery or for "short wire" or rapid exchange (RE) delivery procedures known to those of skill in the art. Accordingly, the delivery catheter housing 72 may be structurally modified with apertures or modified lumenal portions to allow exchange from the angioplasty wire guide to the delivery catheter housing 72 by RE without the need to replace the wire guide with an exchange-length guide wire before exchanging the catheters. Exemplary RE catheters that may be used to deliver the closure device 20 of the present invention are described in U.S. Pat.

Nos. 5,690,642; 5,814,061; 6,371,961; and U.S. Pat. Application Nos. 2005/0070794; 2005/0125050; and 2005/0070821, the disclosures of which are expressly incorporated by reference herein.

To enhance the shelf life of the closure device containing bioremodelable materials, the closure device 20 may be lyophilized in an elongated form inside a cartridge sheath having a similar inner diameter sheath size as the delivery catheter housing 72 (for example, 8-12 French size). In view of their low device profile, closure devices 20 of the present invention can be delivered and securely deployed from a single, tip preloaded delivery catheter for immediate and complete passageway closure in as little as 15 minutes.

Figure 11:
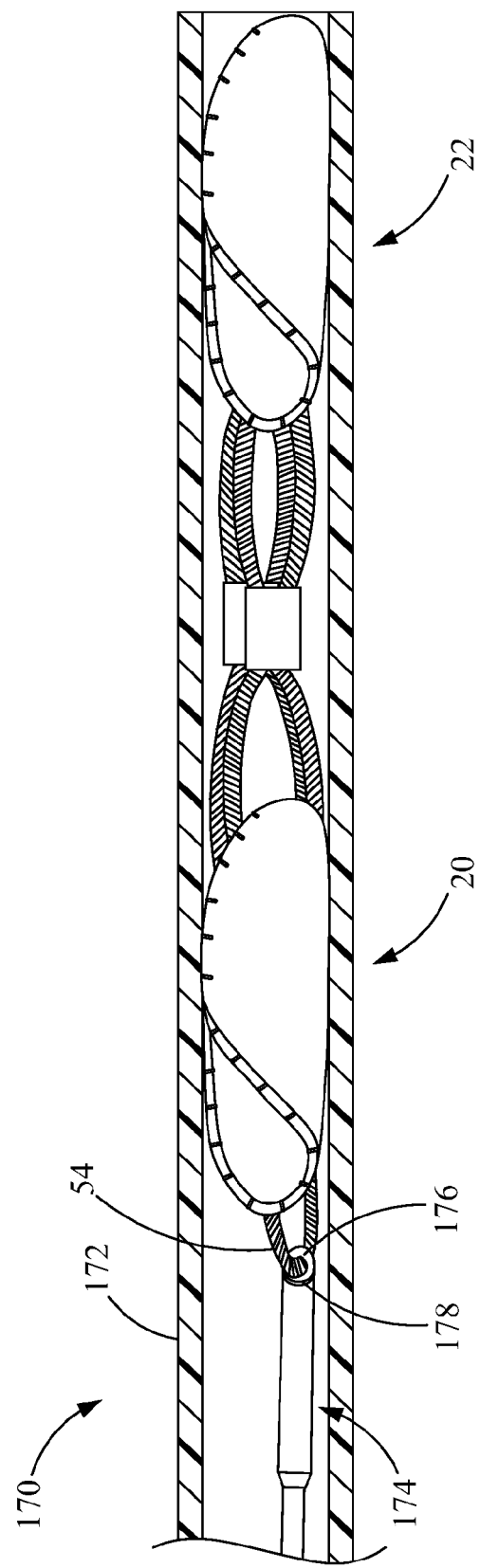
FIG. 11 is a cross-sectional view of the distal end of another closure device assembly, according to the principles of the present invention.
Figure 12:
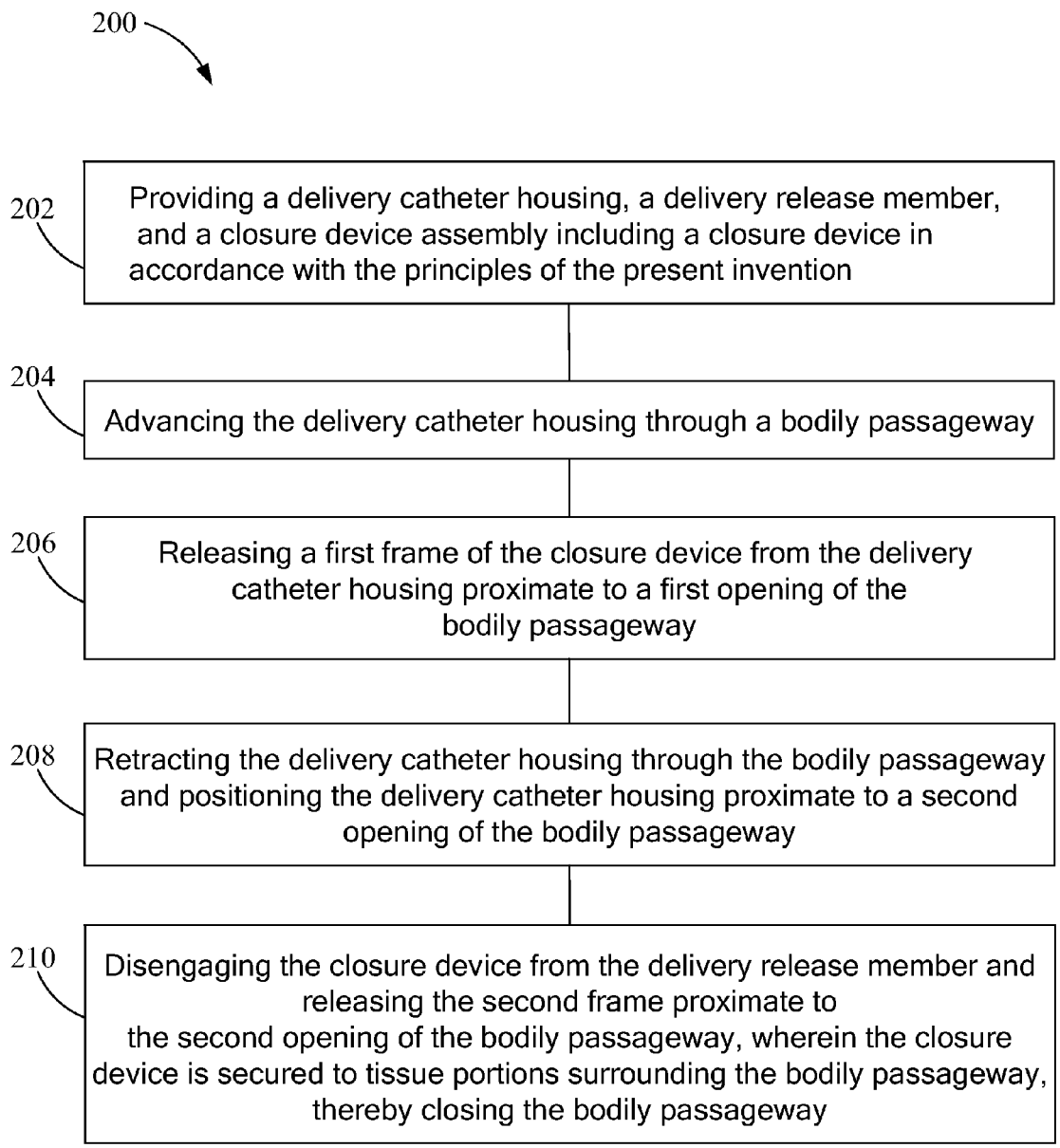
FIG. 12 is a block diagram illustrating a method for closing a bodily passageway in a patient, according to the principles of the present invention.

With reference to FIG. 11, an alternative closure device assembly 170 is illustrated including a preloaded, collapsibly disposed closure device 20, such as the one depicted in FIGS. 2-6. The closure device assembly 170 includes a collapsibly disposed closure device 20 disposed near the distal tip of a delivery catheter 172. The closure device assembly 170 includes a delivery catheter housing 172 and a delivery bar release member 174 in the form of a smaller, coaxially positioned locking catheter 178 connected to a hook 176 that is subject to a spring tension release mechanism. The linkage between the hook 176 and the delivery bar 54 can facilitate accurate placement and uncoupling of the closure device 20 from the delivery catheter 72 in connection with closure device 20 deployment.

The distal end of the locking catheter 178 includes a hollow cannula overhanging at least a portion of the hook 176, whereby the spring tension release mechanism prevents premature disengagement of the delivery bar 54 from the hook 176 in the tip-preloaded closure device 20 or following retraction of the delivery catheter 172 or following extension of the locking catheter 178 out of the delivery catheter 172 during delivery of the device.

In one embodiment, the Gunther Tulip™ Vena Cava filter delivery system (Cook Inc., Bloomington, Ind.) provides an exemplary locking catheter 178 (a metal cannula in this case) for releasable attachment and delivery of closure devices 20, including those configured to include a delivery bar 54 as described above. Components in the Gunther Tulip Vena Cava filter delivery system, including the hook, delivery sheath, or locking catheter, can be shape-modified or size-modified to accommodate a variety of closure device sizes or grasping members, including delivery bars 54 or other portions of the closure device 20.

In a further aspect, referring to FIGS. 10A-10C and FIG. 12, the present invention provides a method for closing or occluding a bodily opening in a patient using any variation of the above described closure device 20 or closure device assemblies 70, 170. In a preferred embodiment, a method 200 for closing or occluding a septal opening, such as a PFO using a closure device assembly is provided herein.

By way of example, FIGS. 10A-10C depict an exemplary method for closing a PFO with an exemplary closure device assembly 70. An exemplary method 200 for delivering any variation of the above-described closure device 20 includes a step 202 of providing a closure device assembly 70, including a delivery catheter housing 72, a delivery release member 74, and a closure device 20 in accordance with the principles of a present invention described herein. The method 200 may further include passing a stiff guide wire through a suitable multi-purpose catheter and positioning the guide wire in the left atrium 4 across a bodily passageway, such as a PFO.

The delivery catheter housing 72 of the closure device assembly 70 is then introduced over the wire (not shown) into the patient. The method 200 includes a step 204 of advancing the delivery catheter housing 72 through a bodily passageway. Accordingly, the delivery catheter housing 72 is advanced through a bodily passageway, depicted here as a PFO having an opening 9 between a septum primum 7 and a septum secundum 8, and the delivery catheter 72 is positioned into the left atrium 4 of a patient. Before releasing the closure device 20 or any part thereof, its position may be assessed by contrast media injection though the delivery catheter housing 72, by way of example.

The method 200 further includes a step 206 of releasing a first frame 22 of the closure device 20 from the delivery catheter housing 72 proximate to the first opening 9' of the bodily passageway 9. Following confirmation of left atrium 4 positioning, in this embodiment, the covered first frame 22 is released from the delivery catheter housing 72 into the left atrium 4 proximate to the distal first opening 9' of the PFO. This may be performed by beginning to retract the delivery catheter housing 72 into the opening 9.

The method 200 includes a step 208 of retracting the delivery catheter housing 72 through the bodily passageway 9 and positioning the delivery catheter housing 72 proximate to a second opening 9" of the bodily passageway 9. Therefore, following release of the covered first frame 22 from the distal end of the delivery catheter housing 72, the delivery catheter housing 72 is retracted through the PFO passageway 9. The crossbars 34, 36, 38, 40 may be partially or fully released into the opening 9 during the retraction of the delivery catheter housing 72 through the opening 9. After being retracted through the opening 9, the delivery catheter housing 72 is positioned in the right atrium 2 near the proximal second opening 9" of the PFO.

The method 200 further includes a step 210 of disengaging the closure device 20 from the delivery release member 74 and releasing the second frame 24 to release the closure device 20 proximate to the second opening 9" of the bodily passageway 9, wherein the closure device 20 is secured to tissue portions 7, 8 surrounding the bodily passageway 9, thereby closing the bodily passageway 9. Accordingly, following proper confirmation of right atrium 2 closure device 20 positioning, the locking catheter sheath 78 may be pulled back to disengage the engaging structure 76 of the delivery release member 74 from the delivery bar 54 connected to the second frame 24, thereby releasing the anchor delivery bar 54 and second frame 24 into the right atrium 2 near the proximal second opening 9" of the PFO 9. Alternatively, when a locking catheter is not used, the delivery catheter housing 72 may be retracted to release the delivery bar 54 and/or the second frame 24 from the end of the delivery catheter housing 72.

The closure device 20 is preferably self-expanding and retains its original expanded shape following release. For example, upon release from the delivery catheter housing 72, the first and second frames 22, 24 expand, springing back against the septum primum 7 and septum secundum 8 on each side of the PFO 9, thus anchoring the first frame 22, 24 to each side 9', 9" of the PFO 9. The biocompatible sheets 26, 28 covering the first and second frames 22, 24 cover and occlude the PFO 9. The delivery catheter housing 72, locking catheter 78, and biopsy forceps or other engaging device 76 are then removed.

Of course, in the alternative to the method 200, any method for closing a bodily passageway, including PFOs, may be practiced using any of the above-described closure devices 20 or assemblies.

As an alternative to the pre-assembled over-the-wire assembly described above, one can alternatively introduce and position a wire guide through a suitable catheter or sheath near the site of the passageway opening; load the collapsible closure device 20 into the sheath; push the closure device 20 to the desired site with a biopsy forceps, pushing catheter, or other suitable pushing device, for example; and release the closure device 20 as described above.

Visualization of the closure device assembly 70, 170 within the interior of the heart during deployment may be provided by various means. For example, fluoro-visible (or radio-opaque) dyes may be injected into the cardiac chambers and venous anatomy so that the chambers of the heart and the related vasculature are visible using a fluoroscopic device. This procedure, sometimes referred to as a venogram, allows the surgeon to locate a precise site and achieve proper device placement when performing an implant procedure.

Additionally, an ultrasonic probe may be positioned in the patient's esophagus, on the surface of the patient's chest, or in the chest cavity adjacent or in contact with the exterior of the heart to ultrasonically image the interior of the heart. In particular an intravascular ultrasound (IVUS) catheter may be utilized in conjunction with one of the above closure device assemblies 70, 170 to provide ultrasonic imaging. Alternatively, an endoscope with a translucent bulb or balloon over its distal end may be introduced into the heart through the closure device assembly or through a separate incision in the wall of the heart to allow video-based or direct visualization of the interior of the heart. An angioscope introduced into the heart endovascularly through a peripheral vessel may also be used for intracardiac visualization. Fluoroscopy or magnetic resonance imaging (MRI) may provide an additional means for visualization.

Sheaths, dilators, catheters, multi-purpose catheters, pushing catheters, wire guides and needles used in the present invention can all be conventional marketed products or modifications thereof. For example, sheaths can be formed from PTFE (such as Teflon) or polyamide (such as Nylon) material, or a combination of materials such as an assembly including an inner layer of PTFE, a flat wire coil over the PTFE for kink resistance, and a polyamide (Nylon) outer layer to provide integrity to the overall structure and a smooth surface (as in the Flexor® Introducer Sets, Cook Medical Inc., Bloomington, Ind.). Dilators can be made from conventional dilator/catheter type materials such as polyethylene, polyamide, polyurethane or vinyl, or any combination of these materials. Fittings provided for sheath/dilator assemblies can be conventional elements such as luer locks; the dilator and the locking catheter can have fittings allowing them to be locked to the sheath during insertion and manipulation. Catheters can be made from conventional materials such as polyethylene, polyamide, PTFE, polyurethane, and other materials. Assembly components, including biopsy forceps or hooks, may be separately contained in interlumenal sheaths within the delivery catheter or they may be disposed through secondary lumenal portions formed in the delivery catheter, as in double lumen catheters and the like.

The delivery catheter housing 72, 172 includes a sheath having a lumen diameter sized to allow for the introduction of the closure device 20 to occlude the bodily passageway of interest. Illustratively, the inner diameter (I.D.) of the delivery sheath may range from 6 to at least 15 French or more, depending on the size of the closure device and the bodily passageway for closure. In preferred embodiments the delivery catheter housing 72, 172 includes an inner diameter of 6 French (corresponding to an I.D. of about 0.087 inch), 7 French (corresponding to an I.D. of about 0.100 inch), 8 French (corresponding to an I.D. of about 0.113 inch), 12 French (corresponding to an I.D. of about 0.162 inch), and 15 French (corresponding to an I.D. of about 0.197 inch).

A closure device 20 or assembly 70, 170 according to the present invention is particularly suited for closing septal heart defects, including PFOs and other atrial septal or ventricular septal defects. However, the closure device 20 can be similarly applied to closing or occluding a variety of other heart openings, tissue openings, vessels, vessel punctures, ducts, and other tissue openings where closure is desired.

In some instances it may be necessary to reposition or remove the closure device 20, particularly when it includes sufficiently flexible materials or a sufficiently flexible structural configuration. This may occur where the device is not appropriately positioned or sized for a particular bodily passageway and/or fails to completely seal the passageway. In cases where it is necessary or advisable to reposition the closure device 20 following initiation of deployment or prior to full deployment, a delivery release member 74, 174 may be used to reposition the device. In this case, a delivery release member 74, 174 remaining connectively linked to a delivery bar 54 or a frame 22, 24 or crossbar 34, 36, 38, 40 may be pushed back into the side of the bodily passageway holding the closure device 20 and pulled back into the delivery sheath, at which point repositioning of the closure device 20 can be initiated prior to full deployment (and release).

In cases where it is necessary or advisable to remove the closure device 20 following full deployment, a suitable foreign body retrieval device, such as a snare, may be used to remove the device. The snare may be delivered through the introducer sheath using a snare catheter. Preferred snares are commercially available under the trade names Needle's Eye® Snare (Cook Medical, Bloomington, Ind.) and Microvena Amplatz Goose Neck® Snare (ev3 Inc., Plymouth, Minn.). After positioning the snare around the delivery bar 54 and advancing the delivery bar 54 through the passageway 9 where the covered first frame 22 is held, the closure device 20 can be pulled back into a delivery catheter sheath and removed.

In some applications, it is advisable to measure the size of the bodily opening prior to installation of the closure device 20. Measurement may be made using a balloon catheter, for example. Further, in some applications, it may be advisable to enlarge the bodily passageway before closing it with a closure device 20. An angioplasty balloon and/or an occlusion balloon may be inflated within the interatrial septum to enlarge the opening, by way of example, and to measure the size of the opening.

It is intended that the foregoing detailed description be regarded as illustrative rather than limiting, and that it be understood that it is the following claims, including all equivalents, that are intended to define the spirit and scope of this invention.

Although the embodiments of this device have been disclosed as being constructed from wire having a round cross section, it could also be cut from a tube of suitable material by laser cutting, electrical discharge machining or any other suitable process.

While the present invention has been described in terms of preferred embodiments, it will be understood, of course, that the invention is not limited thereto since modifications may be made to those skilled in the art, particularly in light of the foregoing teachings.

What is claimed is:

1. A method for closing a bodily passageway in a patient, the method comprising:
   providing a closure device assembly, the closure device assembly comprising:
   a delivery catheter housing;
   a delivery release member; and a collapsibly disposed closure device, the closure device comprising:
a first frame comprising at least one hollow tube;
a sheet of biocompatible material attached to the first frame;
a first crossbar extending across the first frame, the first crossbar having terminal crossbar ends connectively linked to separate sites on the first frame;
a second crossbar attached to the first crossbar at a connection point; and
a second frame comprising at least one hollow tube, the second crossbar extending across the second frame, the second crossbar having terminal crossbar ends connectively linked to separate sites on the second frame,
wherein the first crossbar and the second crossbar each comprise at least one hollow tube and are each configured to bend away from the connection point when the closure device is deployed to close a bodily passageway;
wherein at least one first retention member extends through a lumen of the hollow tube of the first frame and connects the first crossbar to the first frame,
wherein at least one second retention member extends through a lumen of the hollow tube of the second frame and connects the second crossbar to the second frame;
advancing the delivery catheter housing through the bodily passageway;
releasing the first frame from the delivery catheter housing proximate to a first opening of the bodily passageway;
retracting the delivery catheter housing through the bodily passageway and positioning the delivery catheter housing proximate to a second opening of the bodily passageway; and
disengaging the closure device from the delivery release member and releasing the second frame proximate to the second opening of the bodily passageway,
wherein the closure device is secured to tissue portions surrounding the bodily passageway, thereby closing the bodily passageway.

2. The method of claim 1, wherein the closure device further comprises a third crossbar and a fourth crossbar, the third crossbar having terminal crossbar ends connectively linked to separate sites on the first frame, and the fourth crossbar having terminal ends connectively linked to separate sites on the second frame.

3. The method of claim 2, wherein the connection point is a first connection point, and wherein the third crossbar is attached to the fourth crossbar at a second connection point, the third and fourth crossbars being configured to bend away from the second connection point when the closure device is deployed to close a bodily passageway.

4. The method of claim 1, wherein the at least one first retention member is threaded through a lumen of the hollow tube of the first frame and connects the first crossbar to the first frame.

5. A method for making a closure device for closing a bodily passageway, the method comprising:
threading at least one first retention member through at least one first tubular member to create a first frame;
threading the at least one first retention member through a first crossbar and a third crossbar;
fastening the at least one first retention member to hold together the at least one first tubular member, the first crossbar and the third crossbar;
threading at least one second retention member though at least one second tubular member to create a second frame;
threading the at least one second retention member through a second crossbar and a fourth crossbar;
fastening the at least one second retention member to hold together the at least one second tubular member, the second crossbar and the fourth crossbar;
attaching a central portion of the first crossbar to the second crossbar;
attaching a central portion of the third crossbar to the fourth crossbar;
threading at least one third retention member through a delivery bar; and
fastening the at least one third retention member to at least one of the following:
the at least one first tubular member, the at least one second tubular member, the at least one first retention member, and the at least one second retention member.

6. The method of claim 5, wherein the retention members are provided as wires.

7. The method of claim 6, wherein the tubular members, the crossbars, and the delivery bar are provided as coils.

8. The method of claim 7, wherein the step of attaching a central portion of the first crossbar to the second crossbar comprises threading the first crossbar and the second crossbar through a first marker band; and wherein the step of attaching a central portion of the third crossbar to the fourth crossbar comprises threading the third crossbar and the fourth crossbar through a second marker band.

9. A method for making a closure device for closing a bodily passageway, the method comprising:
threading at least one first retention member through at least one first tubular member to create a first frame;
threading the at least one first retention member through a first crossbar and a third crossbar;
fastening the at least one first retention member to hold together the at least one first tubular member, the first crossbar and the third crossbar;
threading at least one second retention member though at least one second tubular member to create a second frame;
threading the at least one second retention member through a second crossbar and a fourth crossbar;
fastening the at least one second retention member to hold together the at least one second tubular member, the second crossbar and the fourth crossbar;
attaching a central portion of the first crossbar to the second crossbar;
attaching a central portion of the third crossbar to the fourth crossbar;
threading at least one third retention member through a delivery bar; and
fastening the at least one third retention member to at least one of the following:
the at least one first tubular member, the at least one second tubular member, the at least one first retention member, and the at least one second retention member;
wherein the retention members are provided as wires;
wherein the tubular members are provided as coils; and
wherein the at least one first tubular member comprises two tubular members, and the first retention member is a single retention member that is threaded through each of the two first tubular members multiple times; and
wherein the at least one second tubular member comprises two tubular members, and the second retention member is a single retention member that is threaded through each of the two second tubular members multiple times.

10. The method of claim 9, further comprising heat treating the tubular members and crossbars.

* * * * *